United States Patent
Gomtsyan et al.

(10) Patent No.: US 7,015,233 B2
(45) Date of Patent: Mar. 21, 2006

(54) FUSED COMPOUNDS THAT INHIBIT VANILLOID SUBTYPE 1 (VR1) RECEPTOR

(75) Inventors: Arthur Gomtsyan, Vernon Hills, IL (US); Erol K. Bayburt, Gurnee, IL (US); John R. Koenig, Chicago, IL (US); Chih-Hung Lee, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 71 days.

(21) Appl. No.: 10/459,925

(22) Filed: Jun. 12, 2003

(65) Prior Publication Data

US 2004/0254188 A1 Dec. 16, 2004

(51) Int. Cl.
*C07D 217/00* (2006.01)
*A61K 31/47* (2006.01)

(52) U.S. Cl. ............ 514/322; 514/310; 514/403; 546/143; 546/199; 548/362.1

(58) Field of Classification Search .......... 514/310, 514/322, 450, 403; 546/143, 199; 548/362.1
See application file for complete search history.

(56) References Cited

U.S. PATENT DOCUMENTS 5,656,634 A * 8/1997 Chang et al. ............ 514/256
6,001,860 A * 12/1999 Hamanaka ............... 514/353

FOREIGN PATENT DOCUMENTS

| EP | 587180 A2 | 3/1994 |
|----|-----------|--------|
| EP | 1256574 A1 | 11/2002 |
| WO | WO 98/50347 A1 * | 12/1998 |
| WO | 03/055484 | 7/2003 |
| WO | 03/055848 | 7/2003 |

OTHER PUBLICATIONS

Berge et al., J. Pharmaceutical Sciences 66:1 et seq. (1977).
Caterina et al., "Impaired nociception and pain sensation in mice lacking the capsaicin receptor," Science 288:306-313 (2000).
Caterina et al., "The capsaicin receptor: a heat-activated ion channel in the pain pathway," Nature 389:816-824 (Oct. 23, 1997).
Caterina et al., "The vanilloid receptor: a molecular gateway to the pain pathway," Annu. Rev. Neurosci. 24:487-517 (2001).
Collier et al., "The abdominal constriction response and its suppression by analgesic drugs in the mouse," Br. J. Pharmacol. Chemother. 32:295-310 (1968).
Davis et al., "Vanilloid receptor-1 is essential for inflammatory thermal hyperalgesia," Nature 405:183-186 (2000).
Fowler, "Intravesical treatment of overactive bladder," Urology 55(Supplement 5A):60-64 (2000).
Hayes et al., "Cloning and functional expression of a human orthologue or rat vanilloid receptor-1", Pain 88:205-215 (2000).
IUPAC 1974 Recommendation for Sction E, Fundamental Sterochemistry, Pure App. Chem. 45:13-30 (1976).
Nolano et al., "Topical capsaicin in humans: parallel loss of epidermal nerve fibers and pain sensation," Pain 81:135-145 (1999).
Poste, et al., Prescott (Ed.) Methods in Cell Biology, Academic Press, New York, N.Y. vol. XIV:33 et seq. (1976).

* cited by examiner

*Primary Examiner*—Zinna Northington Davis
(74) *Attorney, Agent, or Firm*—Gabryleda Ferrari-Dileo

(57) ABSTRACT

Compounds of formula (I)

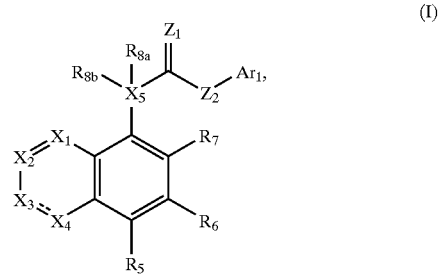

are novel VR1 antagonists that are useful in treating pain, inflammatory thermal hyperalgesia, urinary incontinence, or bladder overactivity.

15 Claims, No Drawings

FUSED COMPOUNDS THAT INHIBIT VANILLOID SUBTYPE 1 (VR1) RECEPTOR

TECHNICAL BACKGROUND

The present invention relates to compounds of formula (I), which are useful for treating disorders caused by or exacerbated by vanilloid receptor activity and pharmaceutical compositions containing compounds of formula (I). The compounds of the present invention are useful in treating pain, bladder overactivity, or urinary incontinence.

BACKGROUND OF INVENTION

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as VR1. The intradermal administration of capsaicin is characterized by an initial burning or hot sensation followed by a prolonged period of analgesia. The analgesic component of VR1 receptor activation is thought to be mediated by a capsaicin induced desensitization of the primary sensory afferent terminal. Thus, the long lasting anti-nociceptive effects of capsaicin has prompted the clinical use of capsaicin analogs as analgesic agents. Further, capsazepine, a capsaicin receptor antagonist can reduce inflammation-induced hyperalgesia in animal models. VR1 receptors are also localized on sensory afferents which innervate the bladder. Capsaicin or resiniferatoxin has been shown to ameliorate incontinence symptoms upon injection into the bladder.

The VR1 receptor has been called a "polymodal detector" of noxious stimuli since it can be activated in several ways. The receptor channel is activated by capsaicin and other vanilloids and thus is classified as a ligand-gated ion channel. VR1 receptor activation by capsaicin can be blocked by the competitive VR1 receptor antagonist, capsazepine. The channel can also be activated by protons. Under mildly acidic conditions (pH 6–7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the VR1 receptor (VR1(−/−)). Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The VR1 (−/−) mice also did not show reduced sensitivity to nerve injury-induced mechanical or thermal nociception. However, the VR1 knock-out mice were insensitive to the noxious effects of intradermal capsaicin, exposure to intense heat (50–55° C.), and failed to develop thermal hyperalgesia following the intradermal administration of carrageenan.

The compounds of the present invention are novel VR1 antagonists and have utility in treating pain, bladder overactivity, or urinary incontinence.

SUMMARY OF THE PRESENT INVENTION

The present invention discloses novel compounds, a method for inhibiting the VR1 receptor in mammals using these compounds, a method for controlling pain in mammals, and pharmaceutical compositions including those compounds. More particularly, the present invention is directed to compounds of formula (I)

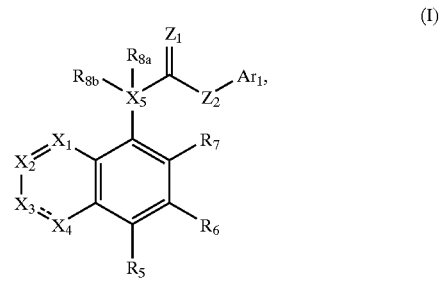

or a pharmaceutically acceptable salt or prodrug thereof, wherein
- - - is absent or a single bond;
$X_1$ is N or $CR_1$;
$X_2$ is N or $CR_2$;
$X_3$ is N, $NR_3$, or $CR_3$;
$X_4$ is a bond, N, or $CR_4$;
$X_5$ is N or C;
provided that at least one of $X_1$, $X_2$, $X_3$, and $X_4$ is N;
$Z_1$ is O, NH, or S;
$Z_2$ is a bond, NH, or O;
$Ar_1$ is dihydro-1H-indenyl, 1H-indenyl, tetrahydronaphthalenyl, or dihydronaphthalenyl, wherein the $Ar_1$ group is optionally substituted with 1, 2, 3, 4, or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, formyl, formylalkyl, haloalkoxy, haloalkyl, haloalkylthio, halogen, heterocycle, hydroxy, hydroxyalkyl, mercapto, mercaptoalkyl, nitro, $(CF_3)_2(HO)C-$, $-NR_AS(O)_2R_B$, $-S(O)_2OR_A$, $-S(O)_2R_B$, $-NZ_AZ_B$, $(NZ_AZ_B)$alkyl, $(NZ_AZ_B)$carbonyl, $(NZ_AZ_B)$carbonylalkyl or $(NZ_AZ_B)$sulfonyl, wherein $Z_A$ and $Z_B$ are each independently hydrogen, alkyl, alkylcarbonyl, formyl, aryl, or arylalkyl;

$R_1$, $R_3$, $R_5$, $R_6$, and $R_7$ are each independently hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C-$, $-NR_AS(O)_2R_B$, $-S(O)_2OR_A$, $-S(O)_2R_B$, $-NZ_AZ_B$, $(NZ_AZ_B)$alkyl, $(NZ_AZ_B)$carbonyl, $(NZ_AZ_B)$carbonylalkyl or $(NZ_AZ_B)$sulfonyl;

R$_2$ and R$_4$ are each independently hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, (CF$_3$)$_2$(HO)C—, —NR$_A$S(O)$_2$R$_B$, —S(O)$_2$OR$_A$, —S(O)$_2$R$_B$, —NZ$_A$Z$_B$, (NZ$_A$Z$_B$)alkyl, (NZ$_A$Z$_B$)alkylcarbonyl, (NZ$_A$Z$_B$)carbonyl, (NZ$_A$Z$_B$)carbonylalkyl, (NZ$_A$Z$_B$)sulfonyl, (NZ$_A$Z$_B$)C(=NH)—, (NZ$_A$Z$_B$)C(=NCN)NH—, or (NZ$_A$Z$_B$)C(=NH)NH—;

R$_A$ is hydrogen or alkyl;

R$_B$ is alkyl, aryl, or arylalkyl;

R$_{8a}$ is hydrogen or alkyl; and

R$_{8b}$ is absent, hydrogen, alkoxy, alkoxycarbonylalkyl, alkyl, alkylcarbonyloxy, alkylsulfonyloxy, halogen, or hydroxy;

provided that R$_{8b}$ is absent when X$_5$ is N.

DETAILED DESCRIPTION OF THE PRESENT INVENTION

In the principle embodiment, compounds of formula (I) are disclosed

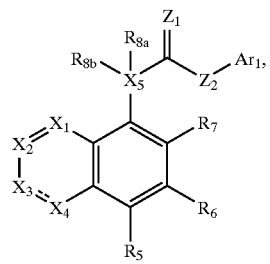

(I)

or a pharmaceutically acceptable salt or prodrug thereof, wherein

- - - is absent or a single bond;

X$_1$ is N or CR$_1$;

X$_2$ is N or CR$_2$;

X$_3$ is N, NR$_3$, or CR$_3$;

X$_4$ is a bond, N, or CR$_4$;

X$_5$ is N or C;

provided that at least one of X$_1$, X$_2$, X$_3$, and X$_4$ is N;

Z$_1$ is O, NH, or S;

Z$_2$ is a bond, NH, or O;

Ar$_1$ is dihydro-1H-indenyl, 1H-indenyl, tetrahydronaphthalenyl, or dihydronaphthalenyl, wherein the Ar$_1$ group is optionally substituted with 1, 2, 3, 4, or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, formyl, formylalkyl, haloalkoxy, haloalkyl, haloalkylthio, halogen, heterocycle, hydroxy, hydroxyalkyl, mercapto, mercaptoalkyl, nitro, (CF$_3$)$_2$(HO)C—, —NR$_A$S(O)$_2$R$_B$, —S(O)$_2$OR$_A$, —S(O)$_2$R$_B$, —NZ$_A$Z$_B$, (NZ$_A$Z$_B$)alkyl, (NZ$_A$Z$_B$)carbonyl, (NZ$_A$Z$_B$)carbonylalkyl or (NZ$_A$Z$_B$)sulfonyl, wherein Z$_A$ and Z$_B$ are each independently hydrogen, alkyl, alkylcarbonyl, formyl, aryl, or arylalkyl;

R$_1$, R$_3$, R$_5$, P6, and R$_7$ are each independently hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, (CF$_3$)$_2$(HO)C—, —NR$_A$S(O)$_2$R$_B$, —S(O)$_2$OR$_A$, —S(O)$_2$R$_B$, —NZ$_A$Z$_B$, (NZ$_A$Z$_B$)alkyl, (NZ$_A$Z$_B$)carbonyl, (NZ$_A$Z$_B$)carbonylalkyl or (NZ$_A$Z$_B$)sulfonyl;

R$_2$ and R$_4$ are each independently hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, (CF$_3$)$_2$(HO)C—, —NR$_A$S(O)$_2$R$_B$, —S(O)$_2$OR$_A$, —S(O)$_2$R$_B$, —NZ$_A$Z$_B$, (NZ$_A$Z$_B$)alkyl, (NZ$_A$Z$_B$)alkylcarbonyl, (NZ$_A$Z$_B$)carbonyl, (NZ$_A$Z$_B$)carbonylalkyl, (NZ$_A$Z$_B$)sulfonyl, (NZ$_A$Z$_B$)C(=NH)—, (NZ$_A$Z$_B$)C(=NCN)NH—, or (NZ$_A$Z$_B$)C(=NH)NH—;

R$_A$ is hydrogen or alkyl;

R$_B$ is alkyl, aryl, or arylalkyl;

R$_{8a}$ is hydrogen or alkyl; and

R$_{8b}$ is absent, hydrogen, alkoxy, alkoxycarbonylalkyl, alkyl, alkylcarbonyloxy, alkylsulfonyloxy, halogen, or hydroxy;

provided that R$_{8b}$ is absent when X$_5$ is N.

In another embodiment of the present invention, compounds of formula (I) are disclosed wherein - - - is a single bond; X$_1$ is CR$_1$; X$_2$ is CR$_2$; X$_4$ is CR$_4$; X$_3$ and X$_5$ are N; Z$_1$ is O; Z$_2$ is NH; Ar$_1$ is dihydro-1H-indenyl optionally substituted with 1, 2, 3, 4, or 5 substituents independently selected from alkenyl, alkoxy, alkoxyalkyl, alkoxycarbonyl, alkyl, alkylcarbonyl, alkylthio, alkynyl, carboxy, cyano, haloalkoxy, haloalkyl, haloalkylthio, halogen, hydroxy, hydroxyalkyl, mercapto, or nitro; R$_{8b}$ is absent; and R$_1$, R$_2$, R$_4$, R$_5$, R$_6$, R$_7$, and R$_{8a}$ are as defined in formula (I).

In another embodiment of the present invention, compounds of formula (I) are disclosed wherein - - - is a single bond; X$_1$ is CR$_1$; X$_2$ is CR$_2$; X$_4$ is CR$_4$; X$_3$ and X$_5$ are N; Z$_1$ is O; Z$_2$ is NH; Ar$_1$ is dihydro-1H-indenyl optionally substituted with 1 or 2 substituents independently selected from alkyl, haloalkyl, or halogen; R$_{8b}$ is absent; and R$_1$, R$_2$, R$_4$, R$_5$, R$_6$, R$_7$, and R$_{8a}$ are as defined in formula (I).

In another embodiment of the present invention, compounds of formula (I) are disclosed wherein - - - is a single bond; X$_1$ is CR$_1$; X$_2$ is CR$_2$; X$_4$ is CR$_4$; X$_3$ and X$_5$ are N; Z$_1$ is O; Z$_2$ is NH; Ar$_1$ is 2,3-dihydro-1H-indenyl optionally substituted with 1 or 2 substituents independently selected from alkyl, haloalkyl, or halogen; R$_{8b}$ is absent; R$_1$, R$_4$, R$_5$, R$_6$, R$_7$, and R$_{8a}$ are hydrogen; and R$_2$ is hydrogen or alkyl.

In another embodiment of the present invention, compounds of formula (I) are disclosed wherein - - - is a single bond; X$_1$ is CRY; X$_2$ is CR$_2$; X$_4$ is CR$_4$; X$_3$ and X$_5$ are N; Z$_1$ is O; Z$_2$ is NH; Ar$_1$ is 2,3-dihydro-1H-inden-1-yl substituted with 1 or 2 substituents independently selected from alkyl, haloalkyl, halogen, or heterocycle wherein the heterocycle is 1-piperidinyl or hexahydro-1H-azepin-1-yl; R$_1$, R$_4$, R$_5$, R$_6$, R$_7$, and R$_{8a}$ are hydrogen; R$_2$ is hydrogen or alkyl; and R$_{8b}$ is absent.

In another embodiment of the present invention, compounds of formula (I) are disclosed wherein - - - is a single bond; X$_1$ is CR$_1$; X$_2$ is CR$_2$; X$_4$ is CR$_4$; X$_3$ and X$_5$ are N; Z$_1$ is O; Z$_2$ is NH; Ar$_1$ is 2,3-dihydro-1H-inden-2-yl substituted with 1 or 2 substituents independently selected from alkyl, haloalkyl, halogen, or heterocycle wherein the heterocycle is 1-piperidinyl or hexahydro-1H-azepin-1-yl; $R_1$, $R_4$, $R_5$, $R_6$, $R_7$, and $R_{8a}$ are hydrogen; $R_2$ is hydrogen or alkyl; and $R_{8b}$ is absent.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 2,3-dihydro-1H-inden-1-yl optionally substituted with 1 or 2 substituents independently selected from alkyl, haloalkyl, halogen, or heterocycle; $R_{8b}$ is absent; and $R_1$, $R_3$, $R_5$, $R_6$, $R_7$, and $R_{8a}$ are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 2,3-dihydro-1H-inden-1-yl optionally substituted with 1 or 2 substituents independently selected from alkyl, haloalkyl, halogen, or heterocycle wherein the heterocycle is piperidinyl or hexahydro-1H-azepinyl; $R_3$ is hydrogen; $R_{8b}$ is absent; and $R_1$, $R_5$, $R_6$, $R_7$, and $R_{8a}$ are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 2,3-dihydro-1H-inden-1-yl optionally substituted with 1 or 2 substituents independently selected from alkyl, haloalkyl, halogen, or heterocycle wherein the heterocycle is piperidinyl or hexahydro-1H-azepinyl; $R_3$ is hydrogen; $R_{8b}$ is absent; and $R_1$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 2,3-dihydro-1H-inden-1-yl optionally substituted with 1 alkyl substituent wherein a preferred alkyl is tert-butyl; $R_3$ is hydrogen; $R_{8b}$ is absent; and $R_1$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 2,3-dihydro-1H-inden-1-yl optionally substituted with 1 heterocycle substituent wherein a preferred heterocycle is 1-piperidinyl or hexahydro-1H-azepin-1-yl; $R_3$ is hydrogen; $R_{8b}$ is absent; and $R_1$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 2,3-dihydro-1H-inden-1-yl optionally substituted with 1 haloalkyl substituent wherein a preferred haloalkyl is trifluoromethyl; $R_3$ is hydrogen; $R_{8b}$ is absent; and $R_4$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $Z_1$ is O; $Z_2$ is NH; $Ar_1$ is 2,3-dihydro-1H-inden-1-yl optionally substituted with 1 or 2 substituents independently selected from alkyl, haloalkyl, halogen, or heterocycle wherein the heterocycle is piperidinyl or hexahydro-1H-azepinyl; $R_3$ is alkoxycarbonyl; $R_{8b}$ is absent; and $R_1$, $R_5$, $R_6$, $R_7$, and $R_{8a}$ are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $Z_1$ is O; $Z_2$ is NH; $Ar_1$ is 2,3-dihydro-1H-inden-1-yl optionally substituted with 1 or 2 substituents independently selected from alkyl, haloalkyl, halogen, or heterocycle wherein the heterocycle is piperidinyl or hexahydro-1H-azepinyl; $R_3$ is alkoxycarbonyl wherein a preferred alkoxycarbonyl is methylcarbonyl, ethylcarbonyl, isopropylcarbonyl, or isobutylcarbonyl; $R_{8b}$ is absent; and $R_1$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $Z_1$ is O; $Z_2$ is NH; $Ar_1$ is 2,3-dihydro-1H-inden-1-yl optionally substituted with 1 alkyl substituent wherein a preferred alkyl is tert-butyl; $R_3$ is alkoxycarbonyl wherein a preferred alkoxycarbonyl is methylcarbonyl, ethylcarbonyl, isopropylcarbonyl, or isobutylcarbonyl; $R_{8b}$ is absent; and $R_1$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $Z_1$ is O; $Z_2$ is NH; $Ar_1$ is 2,3-dihydro-1H-inden-1-yl optionally substituted with 1 haloalkyl substituent wherein a preferred haloalkyl is trifluoroalkyl; $R_3$ is alkoxycarbonyl wherein a preferred alkoxycarbonyl is methylcarbonyl, ethylcarbonyl, isopropylcarbonyl, or isobutylcarbonyl; $R_{8b}$ is absent; and $R_1$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $Z_1$ is O; $Z_2$ is NH; $Ar_1$ is 2,3-dihydro-1H-inden-1-yl optionally substituted with 1 heterocycle substituent wherein a preferred heterocycle is 1-piperidinyl or hexahydro-1H-azepin-1-yl; $R_3$ is alkoxycarbonyl wherein a preferred alkoxycarbonyl is methylcarbonyl, ethylcarbonyl, isopropylcarbonyl, or isobutylcarbonyl; $R_{8b}$ is absent; and $R_1$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 2,3-dihydro-1H-inden-2-yl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_3$, $R_5$, $R_6$, $R_7$, and $R_{8a}$ are hydrogen.

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is 1H-indenyl optionally substituted with 1, 2, 3, 4, or 5 substituents independently selected from alkenyl, alkoxy, alkoxyalkyl, alkoxycarbonyl, alkyl, alkylcarbonyl, alkylthio, alkynyl, carboxy, cyano, haloalkoxy, haloalkyl, haloalkylthio, halogen, hydroxy, hydroxyalkyl, mercapto, or nitro; $R_{8b}$ is absent; and $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is 1H-indenyl optionally substituted with 1 or 2 substituents independently selected from alkyl, haloalkyl, halogen, or heterocycle wherein the heterocycle is 1-piperidinyl or hexahydro 1H-azepin-1-yl; $R_{8b}$ is absent; and $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is 1H-indenyl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_4$, $R_5$, $R_6$, $R_7$, and $R_{8a}$ are hydrogen; and $R_2$ is hydrogen or alkyl.

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is 1H-inden-2-yl substituted with 1 or 2 substituents independently selected from alkyl, haloalkyl, halogen, or heterocycle wherein the heterocycle is 1-piperidinyl or hexahydro-1H-azepin-1-yl; $R_1$, $R_4$, $R_5$, $R_6$, $R_7$, and $R_{8a}$ are hydrogen; $R_2$ is hydrogen or alkyl; and $R_{8b}$ is absent.

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is 1H-inden-3-yl substituted with 1 or 2 substituents independently selected from alkyl, haloalkyl, halogen, or heterocycle wherein the heterocycle is 1-piperidinyl or hexahydro-1H-azepin-1-yl; $R_1$, $R_4$, $R_5$, $R_6$, $R_7$, and $R_{8a}$ are hydrogen; $R_2$ is hydrogen or alkyl; and $R_{8b}$ is absent.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 1H-indenyl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; and $R_1$, $R_3$, $R_5$, $R_6$, $R_7$, and $R_{8a}$ are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 1H-inden-2-yl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_3$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 1H-inden-3-yl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_3$, $R_5$, $R_6$, $R_7$, and $R_{8a}$ are hydrogen.

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is tetrahydronaphthalenyl optionally substituted with 1, 2, 3, 4, or 5 substituents independently selected from alkenyl, alkoxy, alkoxyalkyl, alkoxycarbonyl, alkyl, alkylcarbonyl, alkylthio, alkynyl, carboxy, cyano, haloalkoxy, haloalkyl, haloalkylthio, halogen, hydroxy, hydroxyalkyl, mercapto, or nitro; $R_{8b}$ is absent; and $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is tetrahydronaphthalenyl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; and $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is tetrahydronaphthalenyl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_4$, $R_5$, $R_6$, $R_7$, and $R_{8a}$ are hydrogen; and $R_2$ is hydrogen or alkyl.

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is 1,2,3,4-tetrahydronaphthalen-1-yl substituted with 1 or 2 substituents independently selected from alkyl, haloalkyl, halogen, or heterocycle wherein the heterocycle is 1-piperidinyl or hexahydro-1H-azepin-1-yl; $R_1$, $R_4$, $R_5$, $R_6$, $R_7$, and $R_{8a}$ are hydrogen; $R_2$ is hydrogen or alkyl; and $R_{8b}$ is absent.

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is 1,2,3,4-tetrahydronaphthalen-2-yl substituted with 1 or 2 substituents independently selected from alkyl, haloalkyl, halogen, or heterocycle wherein the heterocycle is 1-piperidinyl or hexahydro-1H-azepin-1-yl; $R_1$, $R_4$, $R_5$, $R_6$, $R_7$, and $R_{8a}$ are hydrogen; $R_2$ is hydrogen or alkyl; and $R_{8b}$ is absent.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is tetrahydronaphthalenyl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; and $R_1$, $R_3$, $R_5$, $R_6$, $R_7$, and $R_{8a}$ are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 1,2,3,4-tetrahydronaphthalen-1-yl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_3$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 1,2,3,4-tetrahydronaphthalen-2-yl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_3$, $R_5$, $R_6$, $R_7$, and $R_{8a}$ are hydrogen.

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is dihydronaphthalenyl optionally substituted with 1, 2, 3, 4, or 5 substituents independently selected from alkenyl, alkoxy, alkoxyalkyl, alkoxycarbonyl, alkyl, alkylcarbonyl, alkylthio, alkynyl, carboxy, cyano, haloalkoxy, haloalkyl, haloalkylthio, halogen, hydroxy, hydroxyalkyl, mercapto, or nitro; $R_{8b}$ is absent; and $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is dihydronaphthalenyl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; and $R_1$, $R_2$, $R_4$, $R_5$, $R_6$, $R_7$, and $R_{8a}$ are as defined in formula (I).

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is dihydronaphthalenyl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_4$, $R_5$, $R_6$, $R_7$, and $R_{8a}$ are hydrogen; and $R_2$ is hydrogen or alkyl.

In another embodiment of the present invention, compounds of formula (I) are disclosed wherein - - - is a single bond; $X_1$ is $CR_1$; $X_2$ is $CR_2$; $X_4$ is CR; $X_3$ and $X_5$ are N; $Z_1$ is O; $Z_2$ is NH; $Ar_1$ is 3,4-dihydronaphthalen-1-yl substituted with 1 or 2 substituents independently selected from alkyl, haloalkyl, halogen, or heterocycle wherein the heterocycle is 1-piperidinyl or hexahydro-1H-azepin-1-yl; $R_1$, $R_4$, $R_5$, $R_6$, $R_7$, and $R_{8a}$ are hydrogen; $R_2$ is hydrogen or alkyl; and $R_{8b}$ is absent.

In another embodiment of the present invention, compounds of formula (I) are disclosed wherein - - - is a single bond; $X_1$ is $CR_1$; $X_2$ is $CR_2$; $X_4$ is CR; $X_3$ and $X_5$ are N; $Z_1$ is O; $Z_2$ is NH; $Ar_1$ is 3,4-dihydronaphthalen-2-yl substituted with 1 or 2 substituents independently selected from alkyl, haloalkyl, halogen, or heterocycle wherein the heterocycle is 1-piperidinyl or hexahydro-1H-azepin-1-yl; $R_1$, $R_4$, $R_5$, $R_6$, $R_7$, and $R_{8a}$ are hydrogen; $R_2$ is hydrogen or alkyl; and $R_{8b}$ is absent.

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is 1,2-dihydronaphthalen-1-yl substituted with 1 or 2 substituents independently selected from alkyl, haloalkyl, halogen, or heterocycle wherein the heterocycle is 1-piperidinyl or hexahydro-1H-azepin-1-yl; $R_1$, $R_4$, $R_5$, $R_6$, $R_7$, and $R_{8a}$ are hydrogen; $R_2$ is hydrogen or alkyl; and $R_{8b}$ is absent.

In another embodiment of the present invention, compounds of formula (I) are disclosed wherein - - - is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is 1,2-dihydronaphthalen-2-yl substituted with 1 or 2 substituents independently selected from alkyl, haloalkyl, halogen, or heterocycle wherein the heterocycle is 1-piperidinyl or hexahydro-1H-azepin-1-yl; $R_1$, $R_4$, $R_5$, $R_6$, $R_7$, and $R_{8a}$ are hydrogen; $R_2$ is hydrogen or alkyl; and $R_{8b}$ is absent.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is dihydronaphthalenyl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; and $R_1$, $R_3$, $R_5$, $R_6$, $R_7$, and $R_{8a}$ are as defined in formula (I).

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 3,4-dihydronaphthalen-1-yl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_3$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 3,4-dihydronaphthalen-2-yl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_3$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 1,2-dihydronaphthalen-1-yl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_3$, $R_5$, $R_6$, $R_7$, and $R_{8a}$ are hydrogen.

In another embodiment of the present invention, compounds of formula (I) are disclosed wherein - - - is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is 1,2-dihydronaphthalen-2-yl optionally substituted with 1 or 2 substituents independently selected from alkyl, haloalkyl, halogen, or heterocycle wherein the heterocycle is 1-piperidinyl or hexahydro-1H-azepin-1-yl; $R_{8b}$ is absent; $R_1$, $R_3$, $R_5$, $R_6$, $R_7$, and $R_{8a}$ are hydrogen.

Another embodiment of the present invention relates to pharmaceutical compositions comprising a therapeutically effective amount of a compound of formula (I) or a pharmaceutically acceptable salt or prodrug thereof.

Another embodiment of the present invention relates to a method for treating a disorder wherein the disorder is ameliorated by inhibiting vanilloid receptor subtype 1 (VR1) in a mammal comprising administering a therapeutically effective amount of a compound of formula (I) or a pharmaceutically acceptable salt or prodrug thereof.

Another embodiment of the present invention relates to a method for treating pain in a mammal comprising administering a therapeutically effective amount of a compound of formula (I) or a pharmaceutically acceptable salt or prodrug thereof.

Another embodiment of the present invention relates to a method for treating urinary incontinence in a mammal comprising administering a therapeutically effective amount of a compound of formula (I) or a pharmaceutically acceptable salt or prodrug thereof.

Another embodiment of the present invention relates to a method for treating bladder overactivity in a mammal comprising administering a therapeutically effective amount of a compound of formula (I) or a pharmaceutically acceptable salt or prodrug thereof.

Another embodiment of the present invention relates to a method for treating inflammatory thermal hyperalgesia in a mammal comprising administering a therapeutically effective amount of a compound of formula (I) or a pharmaceutically acceptable salt or prodrug thereof.

Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through an alkoxy group, as defined herein. Representative examples of alkoxyalkoxy include, but are not limited to, methoxymethoxy, ethoxymethoxy and 2-ethoxyethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "$Ar_1$" as used herein, means an aryl group selected from dihydro-H-indenyl, 1H-indenyl, tetrahydronaphthalenyl, or dihydronaphthalenyl. The $Ar_1$ group is attached to the parent molecular moiety via any position. Representative examples include, but are not limited to, 2,3-dihydro-1H-inden-1-yl, 2,3-dihydro-1H-inden-2-yl, 2,3-dihydro-1H-inden-4-yl, 2,3-dihydro-1H-inden-5-yl, 1H-inden-1-yl, 1H-inden-2-yl, 1H-inden-3-yl, 1H-inden-4-yl, 1H-inden-5-yl, 1,2,3,4-tetrahydro-1-naphthalenyl, 1,2,3,4-tetrahydro-2-naphthalenyl, 1,2,3,4-tetrahydro-5-naphthalenyl, 1,2,3,4-tetrahydro-6-naphthalenyl, 1,2-dihydro-1-naphthalenyl, 1,2-dihydro-2-naphthalenyl, 1,2-dihydro-3-naphthalenyl, 1,2-dihydro-4-naphthalenyl, 1,2-dihydro-5-naphthalenyl, 1,2-dihydro-6-naphthalenyl, 1,2-dihydro-7-naphthalenyl, 1,2-dihydro-8-naphthalenyl, 3,4-dihydronaphthalen-1-yl, and 3,4-dihydronaphthalen-2-yl.

The $Ar_1$ groups of this invention can be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, formyl, formylalkyl, haloalkoxy, haloalkyl, haloalkylthio, halogen, heterocycle, hydroxy, hydroxyalkyl, mercapto, mercaptoalkyl, nitro, $(CF_3)_2(HO)C—$, $—NR_AS(O)_2R_B$, $—S(O)_2OR_A$, $—S(O)_2R_B$, $—NZ_AZ_B$, $(NZ_AZ_B)$alkyl, $(NZ_AZ_B)$carbonyl, $(NZ_AZ_B)$carbonylalkyl or $(NZ_AZ_B)$sulfonyl, wherein $Z_A$ and $Z_B$ are each independently hydrogen, alkyl, alkylcarbonyl, formyl, aryl, or arylalkyl. Representative examples of substituted $Ar_1$ groups include, but are not limited to, 5-tert-butyl-2,3-dihydro-1H-inden-1-yl, 5-tert-butyl-2,3-dihydro-1H-inden-2-yl, 5-bromo-2,3-dihydro-1H-inden-1-yl, (3R)-5-tert-butyl-3-methyl-2,3-dihydro-1H-inden-1-yl, and (3S)-5-tert-butyl-3-methyl-2,3-dihydro-1H-inden-1-yl.

The term "aryl" as used herein, means a phenyl group, or a bicyclic or a tricyclic fused ring system wherein one or more of the fused rings is a phenyl group. Bicyclic fused ring systems are exemplified by a phenyl group fused to a cycloalkyl group, as defined herein, or another phenyl group. Tricyclic fused ring systems are exemplified by a bicyclic fused ring system fused to a cycloalkyl group, as defined herein, or another phenyl group. Representative examples of aryl include, but are not limited to, anthracenyl, azulenyl, fluorenyl, indenyl, naphthyl, phenyl and tetrahydronaphthyl.

The aryl groups of this invention can be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $—NZ_CZ_D$, $(NZ_CZ_D)$alkyl, $(NZ_CZ_D)$carbonyl, $(NZ_CZ_D)$carbonylalkyl, $(NZ_CZ_D)$sulfonyl, $—NR_AS(O)_2R_B$, $—S(O)_2OR_A$ and $—S(O)_2R_A$ wherein $R_A$ and $R_B$ are as defined herein.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "arylthio" as used herein, means an aryl group, as defined herein, appended to the parent molecular moiety through a sulfur atom. Representative examples of arylthio include, but are not limited to, phenylsulfanyl, naphth-2-ylsulfanyl, and 5-phenylhexylsulfanyl.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" as used herein, means a saturated monocyclic ring system containing from 3 to 8 carbon atoms. Examples of cycloalkyl include cyclopropyl, cyclobutyl, cyclopentyl, cyclohexyl, cycloheptyl, and cyclooctyl.

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkylthio" as used herein, means at least one halogen, as defined herein, appended to the parent molecular moiety through an alkylthio group, as defined herein. Representative examples of haloalkylthio include, but are not limited to, trifluoromethylthio.

The term "heterocycle," as used herein, refers to a three, four, five, six, seven, or eight membered ring containing one or two heteroatoms independently selected from the group consisting of nitrogen, oxygen, and sulfur. The three membered ring has zero double bonds. The four and five membered ring has zero or one double bond. The six membered ring has zero, one, or two double bonds. The seven and eight membered rings have zero, one, two, or three double bonds. The heterocycle groups of the present invention can be attached to the parent molecular moiety through a carbon atom or a nitrogen atom. Representative examples of heterocycle include, but are not limited to, azetidinyl, hexahydro-1H-azepinyl, hexahydroazocin-(2H)-yl, morpholinyl, piperazinyl, piperidinyl, pyrrolidinyl, and thiomorpholinyl.

The heterocycles of the present invention are substituted with 0, 1, 2, 3, or 4 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkynyl, arylalkyl, arylalkoxycarbonyl, carboxy, cyano, formyl, haloalkoxy, haloalkyl, halo, hydroxy, hydroxyalkyl, mercapto, and nitro.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —OCH$_2$O— group wherein the oxygen atoms of the methylenedioxy are attached to the parent molecular moiety through two adjacent carbon atoms.

The term "nitro" as used herein, means a —NO$_2$ group.

The term "—NZ$_A$Z$_B$" as used herein, means two groups, Z$_A$ and Z$_B$, which are appended to the parent molecular moiety through a nitrogen atom. Z$_A$ and Z$_B$ are each independently selected from hydrogen, alkyl, alkylcarbonyl, formyl, aryl and arylalkyl. Representative examples of —NZ$_A$Z$_B$ include, but are not limited to, amino, methylamino, acetylamino, benzylamino, phenylamino, and acetylmethylamino.

The term "(NZ$_A$Z$_B$)alkyl" as used herein, means a —NZ$_A$Z$_B$ group, as defined herein, appended to the parent molecular moiety through an alkyl group, as defined herein. Representative examples of (NZ$_A$Z$_B$)alkyl include, but are not limited to, aminomethyl, 2-(methylamino)ethyl, 2-(dimethylamino)ethyl and (ethylmethylamino)methyl.

The term "(NZ$_A$Z$_B$)carbonyl" as used herein, means a —NZ$_A$Z$_B$ group, as defined herein, appended to the parent molecular moiety through a carbonyl group, as defined herein. Representative examples of (NZ$_A$Z$_B$)carbonyl include, but are not limited to, aminocarbonyl, (methylamino)carbonyl, (dimethylamino)carbonyl and (ethylmethylamino)carbonyl.

The term "(NZ$_A$Z$_B$)carbonylalkyl" as used herein, means a (NZ$_A$Z$_B$)carbonyl group, as defined herein, appended to the parent molecular moiety through an alkyl group, as defined herein. Representative examples of (NZ$_A$Z$_B$)carbonylalkyl include, but are not limited to, (aminocarbonyl)methyl, 2-((methylamino)carbonyl)ethyl and ((dimethylamino)carbonyl)methyl.

The term "(NZ$_A$Z$_B$)sulfonyl" as used herein, means a —NZ$_A$Z$_B$ group, as defined herein, appended to the parent molecular moiety through a sulfonyl group, as defined herein. Representative examples of (NZ$_A$Z$_B$)sulfonyl include, but are not limited to, aminosulfonyl, (methylamino)sulfonyl, (dimethylamino)sulfonyl and (ethylmethylamino)sulfonyl.

The term "—NZ$_C$Z$_D$" as used herein, means two groups, Z$_C$ and Z$_D$, which are appended to the parent molecular moiety through a nitrogen atom. Z$_C$ and Z$_D$ are each independently selected from hydrogen, alkyl, alkylcarbonyl, formyl, aryl and arylalkyl. Representative examples of —NZ$_C$Z$_D$ include, but are not limited to, amino, methylamino, acetylamino, benzylamino, phenylamino, and acetylmethylamino.

The term "(NZ$_C$Z$_D$)alkyl" as used herein, means a —NZ$_C$Z$_D$ group, as defined herein, appended to the parent molecular moiety through an alkyl group, as defined herein. Representative examples of (NZ$_C$Z$_D$)alkyl include, but are not limited to, aminomethyl, 2-(methylamino)ethyl, 2-(dimethylamino)ethyl and (ethylmethylamino)methyl.

The term "(NZ$_C$Z$_D$)carbonyl" as used herein, means a —NZ$_C$Z$_D$ group, as defined herein, appended to the parent molecular moiety through a carbonyl group, as defined herein. Representative examples of (NZ$_C$Z$_D$)carbonyl include, but are not limited to, aminocarbonyl, (methylamino)carbonyl, (dimethylamino)carbonyl and (ethylmethylamino)carbonyl.

The term "(NZ$_C$Z$_D$)carbonylalkyl" as used herein, means a (NZ$_C$Z$_D$)carbonyl group, as defined herein, appended to the parent molecular moiety through an alkyl group, as defined herein. Representative examples of (NZ$_C$Z$_D$)carbonylalkyl include, but are not limited to, (aminocarbonyl)methyl, 2-((methylamino)carbonyl)ethyl and ((dimethylamino)carbonyl)methyl.

The term "(NZ$_C$Z$_D$)sulfonyl" as used herein, means a —NZ$_C$Z$_D$ group, as defined herein, appended to the parent molecular moiety through a sulfonyl group, as defined herein. Representative examples of (NZ$_C$Z$_D$)sulfonyl include, but are not limited to, aminosulfonyl, (methylamino)sulfonyl, (dimethylamino)sulfonyl and (ethylmethylamino)sulfonyl.

The term "oxo" as used herein, means =O.

The term "sulfonyl" as used herein, means a —S(O)$_2$— group.

Preferred compounds of the present invention include, but are not limited to,

N-(5-tert-butyl-2,3-dihydro-1H-inden-1-yl)-N'-5-isoquinolinylurea;

N-(5-tert-butyl-2,3-dihydro-1H-inden-1-yl)-N'-(3-methyl-5-isoquinolinyl)urea;

(+) N-(5-tert-butyl-2,3-dihydro-1H-inden-1-yl)-N'-(3-methyl-5-isoquinolinyl)urea;

(−)N-(5-tert-butyl-2,3-dihydro-1H-inden-1-yl)-N'-(3-methyl-5-isoquinolinyl)urea;

(−)N-(5-tert-butyl-2,3-dihydro-1H-inden-1-yl)-N'-5-isoquinolinylurea;

(+) N-(5-tert-butyl-2,3-dihydro-1H-inden-1-yl)-N'-5-isoquinolinylurea;

N-(5-bromo-2,3-dihydro-1H-inden-1-yl)-N'-5-isoquinolinylurea;

methyl 4-({[(5-tert-butyl-2,3-dihydro-1H-inden-1-yl)amino]carbonyl}amino)-1H-indazole-1-carboxylate;

N-(5-tert-butyl-2,3-dihydro-1H-inden-1-yl)-N'-1H-indazol-4-ylurea;

methyl 4-[({[(1S)-5-tert-butyl-2,3-dihydro-1H-inden-1-yl]amino}carbonyl)amino]-1H-indazole-1-carboxylate;

methyl 4-[({[(1R)-5-tert-butyl-2,3-dihydro-1H-inden-1-yl]amino}carbonyl)amino]-1H-indazole-1-carboxylate;

N-[(1S)-5-tert-butyl-2,3-dihydro-1H-inden-1-yl]-N'-1H-indazol-4-ylurea;

N-[(1R)-5-tert-butyl-2,3-dihydro-1H-inden-1-yl]-N'-1H-indazol-4-ylurea;

methyl 4-[({[5-(trifluoromethyl)-2,3-dihydro-1H-inden-1-yl]amino}carbonyl)amino]-1H-indazole-1-carboxylate;

N-1H-indazol-4-yl-N'-[5-(trifluoromethyl)-2,3-dihydro-1H-inden-1-yl]urea;

methyl 4-({[(5-piperidin-1-yl-2,3-dihydro-1H-inden-1-yl)amino]carbonyl}amino)-1H-indazole-1-carboxylate;

N-1H-indazol-4-yl-N'-(5-piperidin-1-yl-2,3-dihydro-1H-inden-1-yl)urea;

methyl 4-({[(5-hexahydro-1H-azepin-1-yl-2,3-dihydro-1H-inden-1-yl)amino]carbonyl}amino)-1H-indazole-1-carboxylate;

N-(5-hexahydro-1H-azepin-1-yl-2,3-dihydro-1H-inden-1-yl)-N'-1H-indazol-4-ylurea;

N-1H-indazol-4-yl-N'-[(1R)-5-piperidin-1-yl-2,3-dihydro-1H-inden-1-yl]urea;

N-1H-indazol-4-yl-N'-[(1S)-5-piperidin-1-yl-2,3-dihydro-1H-inden-1-yl]urea;

isopropyl 4-({[(5-tert-butyl-2,3-dihydro-1H-inden-1-yl)amino]carbonyl}amino)-1H-indazole-1-carboxylate;

isobutyl 4-({[(5-tert-butyl-2,3-dihydro-1H-inden-1-yl)amino]carbonyl}amino)-1H-indazole-1-carboxylate; or a pharmaceutically acceptable salt or prodrug thereof.

Compounds of the present invention can exist as stereoisomers, wherein asymmetric or chiral centers are present. Stereoisomers are designated (R) or (S), depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13–30. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution, a technique well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) direct separation of the mixture of optical enantiomers on chiral chromatographic columns, or (3) formation of a diastereomeric salt followed by selective recrystallization of one of the diastereomeric salts.

Compounds of the present invention were named by ACD/ChemSketch version 5.0 (developed by Advanced Chemistry Development, Inc., Toronto, ON, Canada) or were given names which appeared to be consistent with ACD nomenclature.

Abbreviations

Abbreviations which have been used in the descriptions of the Schemes and the Examples that follow are: atm for atmosphere(s); DBU for 1,8-diazabicyclo[5.4.0]undec-7-ene; DCC for 1,3-dicyclohexylcarbodiimide; DMAP for 4-dimethylaminopyridine; DMF for N,N-dimethylformamide; DMSO for dimethylsulfoxide; EDCI or EDC for 1-ethyl-3-[3-(dimethylamino)propyl]-carbodiimide hydrochloride; Et for CH$_3$CH$_2$; HPLC high pressure liquid chromatography; Me for CH$_3$; Ph for phenyl; psi for pounds per square inch; and THF for tetrahydrofuran.

Preparation of Compounds of the Present Invention

The compounds and processes of the present invention will be better understood in connection with the following synthetic Schemes and Examples which illustrate a means by which the compounds of the present invention can be prepared.

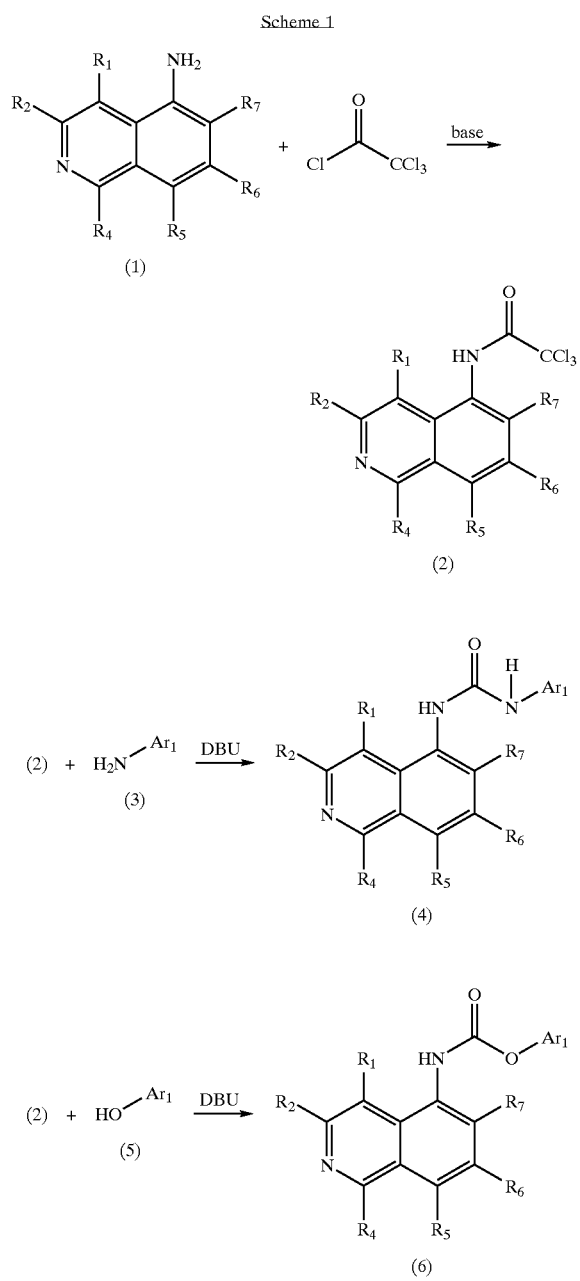

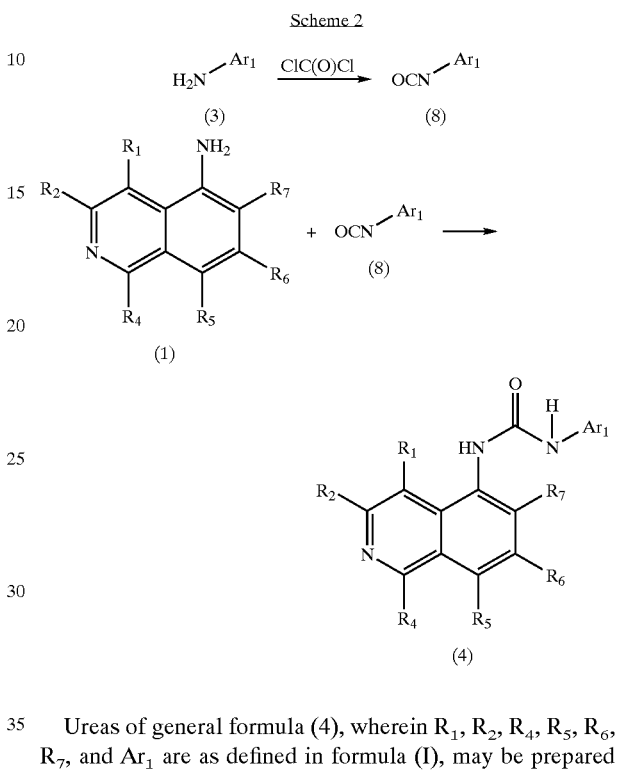

be prepared as described in Scheme 1. Trichloroacetamides of general formula (2) can be treated with alcohols of general formula (5) and a non-nucleophilic base such as, but not limited to, DBU in a solvent such as, but not limited to, acetonitrile to provide carbamates of general formula (6).

Ureas of general formula (4), wherein $R_1$, $R_2$, $R_4$, $R_5$, $R_6$, $R_7$, and $Ar_1$ are as defined in formula (I), may be prepared as described in Scheme 2. Amines of general formula (3) can be treated with phosgene or triphosgene and DMAP in a solvent such as, but not limited to, dichloromethane to provide isocyanates of general formula (8). 5-Aminoisoquinolines of general formula (I) can be treated with isocyanates of general formula (8) in a solvent such as, but not limited to, toluene or THF or a combination thereof to provide ureas of general formula (4).

Ureas of general formula (4), wherein $R_1$, $R_2$, P4, $R_5$, $R_6$, $R_7$, and $Ar_1$ are as defined in formula (1), may be prepared as described in Scheme 1. 5-Aminoisoquinolines of general formula (1), purchased commercially or prepared using standard chemistry known to those in the art, can be treated with trichloroacetyl chloride and a base such as, but not limited to, triethylamine in a solvent such as dichloromethane to provide trichloroacetamides of general formula (2). Trichloroacetamides of general formula (2) can be treated with amines of general formula (3) and a non-nucleophilic base such as, but not limited to, DBU in a solvent such as, but not limited to, acetonitrile to provide ureas of general formula (4).

Carbamates of general formula (6), wherein $R_1$, $R_2$, $R_4$, $R_5$, $R_6$, $R_7$, and $Ar_1$ are as defined in formula (I), may also

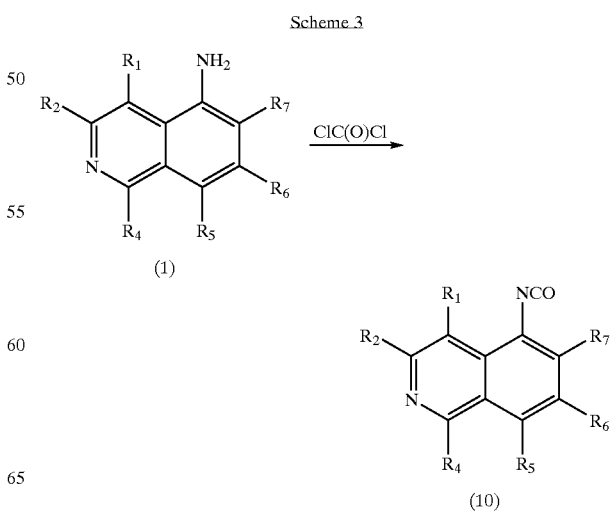

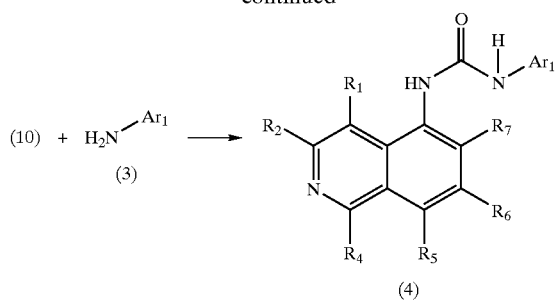

Ureas of general formula (4), wherein $R_1$, $R_2$, $R_4$, $R_5$, $R_6$, $R_7$, and $Ar_1$ are as defined in formula (I), may be prepared as described in Scheme 3. 5-Aminoisoquinolines of general formula (I) can be treated with phosgene or triphosgene and DMAP in a solvent such as, but not limited to, dichloromethane to provide isocyanates of general formula (10). Isocyanates of general formula (10) can be treated with amines of general formula (3) in a solvent such as, but not limited to, toluene or THF or a combination thereof to provide ureas of general formula (4).

Ureas of general formula (20), wherein $R_1$, $R_2$, $R_3$, $R_5$, $R_6$, $R_7$, and $Ar_1$ are as defined in formula (I), and carbamates of general formula (21), wherein $R_1$, $R_2$, $R_3$, $R_5$, $R_6$, $R_7$, and $Ar_1$ are as defined in formula (I), may be prepared as described in Scheme 4. 4-Aminoindoles of general formula (19), purchased commercially or prepared using standard chemistry known to those in the art, may be processed as described in Schemes 1–3 to provide ureas of general formula (20) and carbamates of general formula (21).

Ureas of general formula (23), wherein $R_1$, $R_3$, $R_5$, $R_6$, $R_7$, and $Ar_1$ are as defined in formula (I), and carbamates of general formula (24), wherein $R_1$, $R_3$, $R_5$, $R_6$, $R_7$, and $Ar_1$ are as defined in formula (I), may be prepared as described in Scheme 4. 4-Aminoindazoles of general formula (22), purchased commercially or prepared using standard chemistry known to those in the art, may be processed as described in Schemes 1–3 to provide ureas of general formula (23) and carbamates of general formula (24).

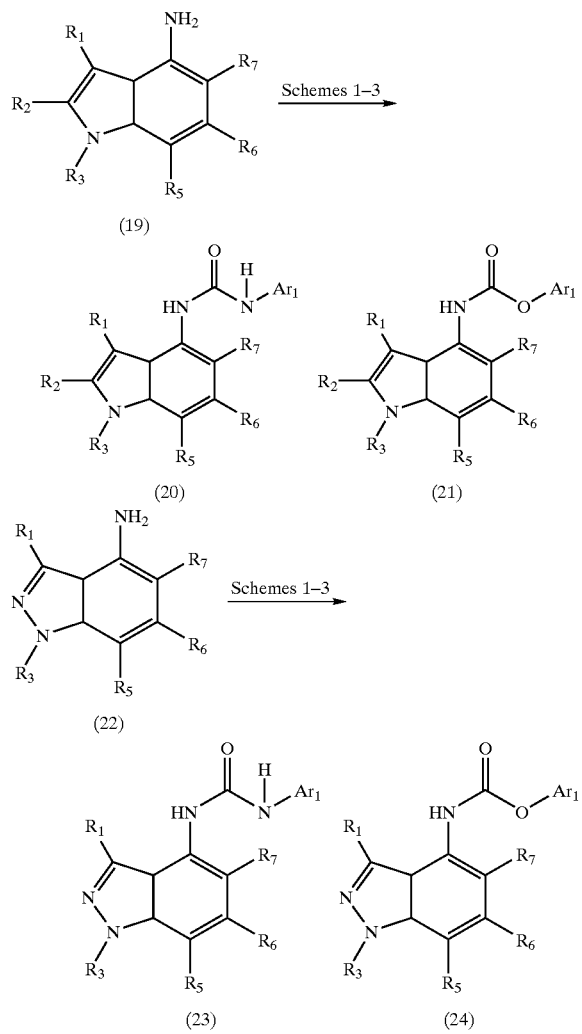

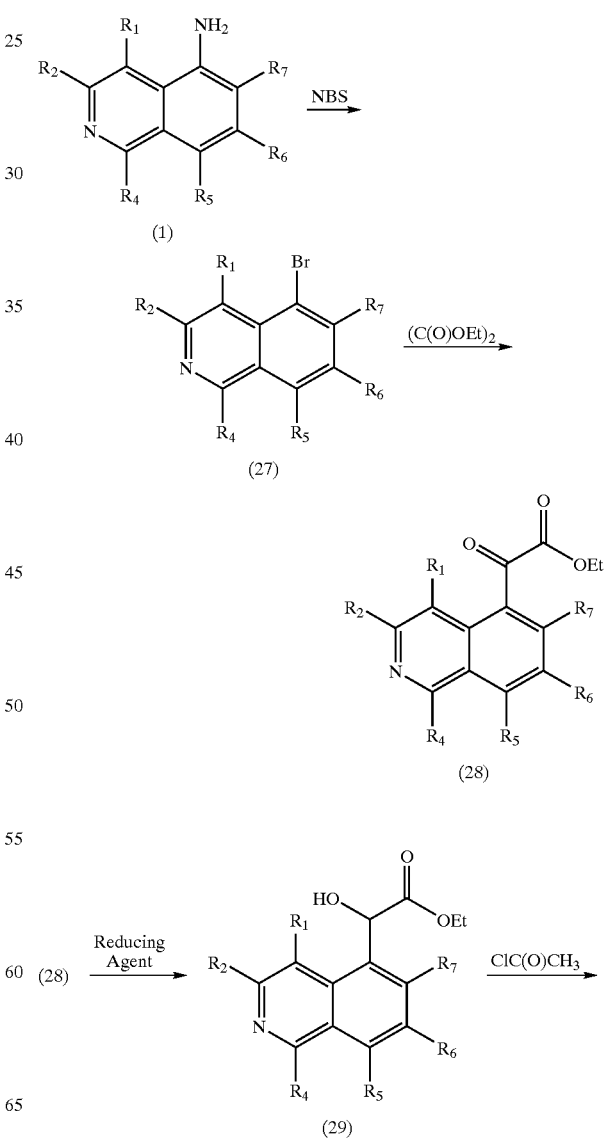

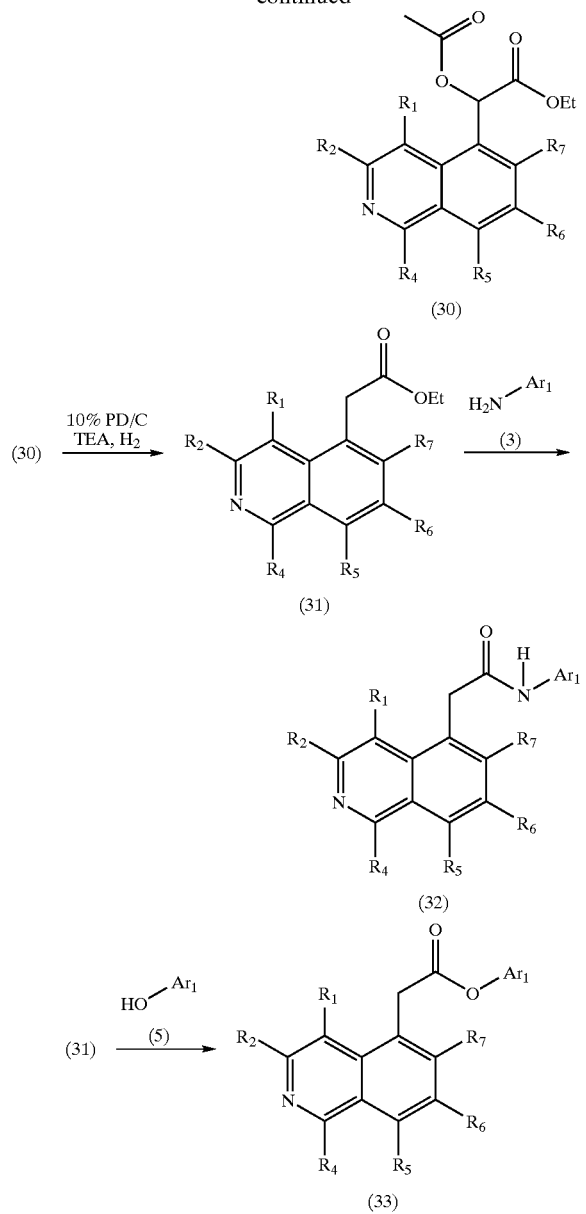

(30) can be treated with 10% Pd/C and a base such as, but not limited to, triethylamine under a hydrogen atmosphere (60 psi) in a solvent such as, but not limited to, ethanol to provide esters of general formula (31). Esters of general formula (31) can be treated with amines of general formula (3) to provide amides of general formula (32). Alternatively, esters of general formula (31) can be treated with aqueous base such as, but not limited to, aqueous sodium hydroxide or aqueous potassium hydroxide to provide the acids which can then be converted into amides of general formula (32) by treatment with amines of general formula (3) under standard DCC or EDCI coupling procedures that are well known in the art.

Esters of general formula (33), wherein $R_1$, $R_2$, $R_4$, $R_5$, $R_6$, $R_7$, and $Ar_1$ are as defined in formula (I), can be prepared as described in Scheme 5. Esters of general formula (31) can be treated with alcohols of general formula (5) under standard transesterification conditions well known to those of skill in the art to provide esters of general formula (33).

Scheme 6

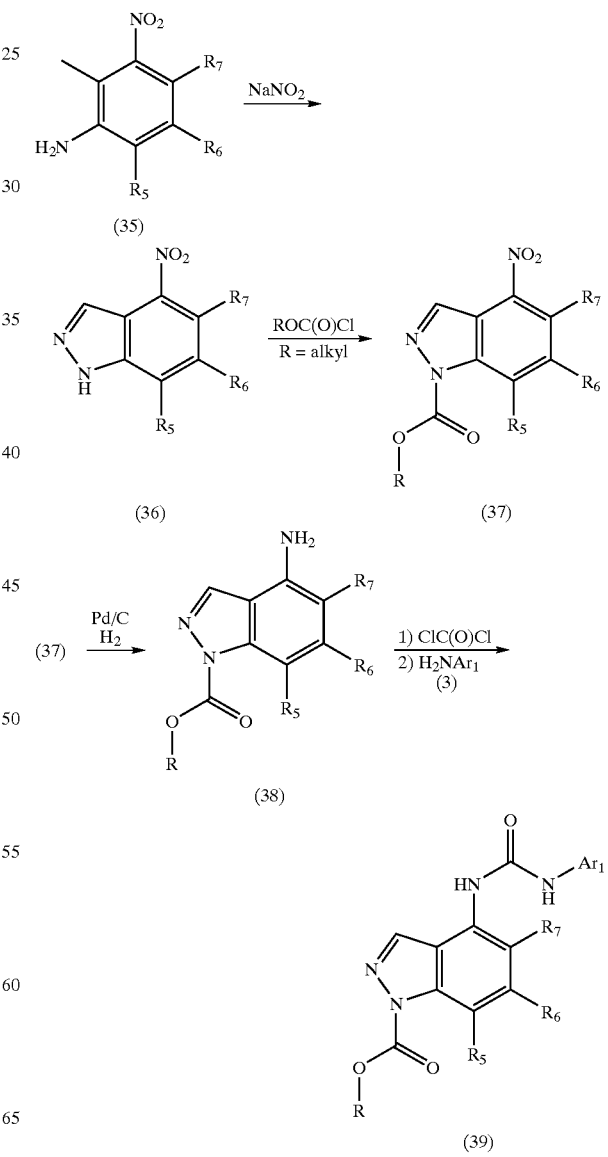

Amides of general formula (32), wherein $R_1$, $R_2$, $R_4$, $R_5$, $R_6$, $R_7$, and $Ar_1$ are as defined in formula (I), can be prepared as described in Scheme 5. Amines of general formula (1) can be treated with an acid such as, but not limited to, concentrated sulfuric acid and N-bromosuccinimide (NBS) to provide bromides of general formula (27). Bromides of general formula (27) can be treated with an organolithium reagent such as, but not limited to, n-butyllithium and diethyl oxalate in a solvent such as, but not limited to, THF to provide keto esters of general formula (28). Keto esters of general formula (28) can be treated with a reducing agent such as, but not limited to, 10% Pd/C under a hydrogen atmosphere (50 psi) in a solvent such as, but not limited to, ethanol to provide hydroxy esters of general formula (29). Hydroxy esters of general formula (29) can be treated with an acid chloride such as, but not limited to, acetyl chloride in a solvent such as, but not limited to, pyridine to provide diesters of general formula (30). Diesters of general formula

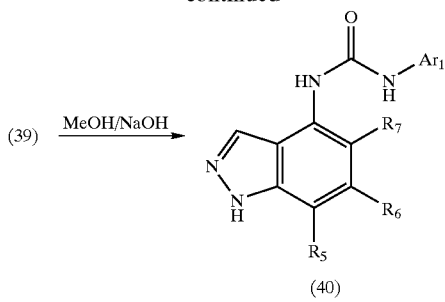

Ureas of general formula (39) and ureas of general formula (40), wherein $R_5$, $R_6$, $R_7$, and $Ar_1$ are as defined in formula (I) and R is alkyl as defined herein, can be prepared as described in Scheme 6. Nitro anilines of general formula (35) can be treated with sodium nitrite and an acid including, but not limited to, acetic acid in water to provide indazoles of general formula (36). Indazoles of general formula (36) can be treated with chloroformates to provide indazoles of general formula (37). Indazoles of general formula (37) can be treated with a transition metal catalyst including, but not limited to, palladium on carbon under a hydrogen atmosphere (about 1 atm to about 60 atm) to provide indazoles of general formula (38). Indazoles of general formula (38) can be processed as described in Scheme 1–3 to provide indazoles of general formula (39). Indazoles of general formula (39) can be treated with a base including, but not limited to, sodium hydroxide or potassium hydroxide to provide indazoles of general formula (40).

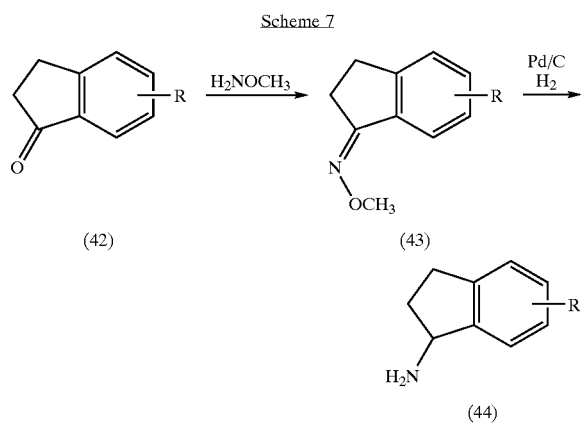

2,3-Dihydro-1H-inden-1-ylamines of general formula (44), wherein R is 1, 2, 3, 4, or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C-$, $-NR_AS(O)_2R_B$, $-S(O)_2OR_A$, $-S(O)_2R_B$, $-NZ_AZ_B$, $(NZ_AZ_B)$alkyl, $(NZ_AZ_B)$carbonyl, $(NZ_AZ_B)$carbonylalkyl or $(NZ_AZ_B)$sulfonyl, wherein $Z_A$ and $Z_B$ are each independently hydrogen, alkyl, alkylcarbonyl, formyl, aryl, or arylalkyl, can be prepared as described in Scheme 7. Indan-1-ones of general formula (42) can be treated with hydroxylamines including, but not limited to, O-methylhydroxylamine to provide oximes of general formula (43). Oximes of general formula (43) can be treated with palladium on carbon under a hydrogen atmosphere (about 1 atm to about 60 atm) to provide 2,3-dihydro-1H-inden-1-ylamines of general formula (44).

The following Examples are intended as an illustration of and not a limitation upon the scope of the invention as defined in the appended claims.

EXAMPLE 1

N-(5-tert-butyl-2,3-dihydro-1H-inden-1-yl)-N'-5-isoquinolinylurea

EXAMPLE 1A 1-(4-tert-butylphenyl)-3-chloro-1-propanone

A solution of tert-butyl benzene (31 ml, 200 mmol) and 3-chloro-propionyl chloride (19 ml, 200 mmol) in methylene chloride (75 ml) was added dropwise to a suspension of aluminum chloride (29.33 g, 220 mmol) in methylene chloride (300 ml) at 0° C. The reaction mixture was allowed to warm to ambient temperature, stirred for 16 hours, and quenched with water dropwise. The reaction mixture was washed with water, dried with magnesium sulfate, and the filtrate was evaporated under reduced pressure to provide the title compound which was used without further purification in the next step.

EXAMPLE 1B 5-tert-butyl-1-indanone 1-(4-tert-Butylphenyl)-3-chloro-1-propanone (22.25 g, 99 mmol) was dissolved in concentrated sulfuric acid (100 ml) and heated on a water bath at 95° C. for 2.5 hours. The reaction mixture was cooled, poured onto ice, and extracted with diethyl ether. The combined organic extracts were washed with saturated aqueous sodium bicarbonate, dried with magnesium sulfate, and the filtrate was evaporated under reduced pressure to provide the title compound which was used without further purification in the next step.

EXAMPLE 1C 5-tert-butyl-1-indanone O-methyloxime 5-tert-Butyl-1-indanone (13.41 g, 71.23 mmol) and methoxyamine hydrochloride (6.68 g, 80 mmol) were disolved in pyridine (75 ml) and stirred at ambient temperature for 16 hours. The mixture was evaporated under reduced pressure and the residue was partitioned between water and diethyl ether (×2). The combined organic layers were washed with 1N aqueous hydrochloric acid, dried with magnesium sulfate, and the filtrate was evaporated under reduced pressure to provide the title compound which was used without further purification in the next step.

EXAMPLE 1D 5-tert-butyl-2,3-dihydro-1H-inden-1-ylamine 5-tert-Butyl-1-indanone O-methyloxime (4.37 g, 20.2 mmol) and 10% palladium on carbon (2.2 g) were combined in methanol (50 ml) and ammonia (10 ml) and placed in a Parr apparatus which was charged with hydrogen to 60 psi.

The reaction was shaken at 50° C. for 16 hours. The reaction mixture was filtered and the filtrate was evaporated under reduced pressure. The residue was treated with diethyl ether (100 ml) and extracted with hydrochloric acid (1N, 3× 50 ml). The combined aqueous extracts were neutralized with sodium hydroxide (6 g) in water (25 ml) and extracted with diethyl ether. The organic extracts were combined, dried with magnesium sulfate, and the filtrate was evaporated under reduced pressure to provide the title compound which was used without further purification in the next step.

EXAMPLE 1E

5-isocyanatoisoguinoline

Phosgene (20 ml, 20% in toluene from Fluka) in $CH_2Cl_2$ (300 mL) at 0° C. was treated with DMAP (10 g) in $CH_2Cl_2$ (100 mL) slowly. After complete addition, the mixture was treated with 5-aminoisoquinoline (5 g) in $CH_2Cl_2$ (100 mL) dropwise. The mixture was allowed to warm to room temperature and then stirred overnight. The solvent was removed under reduced pressure. The solid residue was extracted with diethyl ether (400 mL). The diethyl ether was filtered to provide the title compound in diethyl ether as a pale yellow solution. The diethyl ether solution was used in subsequent reactions without further purification.

EXAMPLE 1F

N-(5-tert-butyl-2,3-dihydro-1H-inden-1-yl)-N'-5-isoguinolinylurea 5-tert-Butyl-2,3-dihydro-1H-inden-1-ylamine (150 mg, 1.13 mmol) in diethyl ether (10 mL) was treated with 5-isocyanatoisoquinoline in diethyl ether. The mixture was stirred for 2 hours, filtered, and the filter cake was washed with diethyl ether to provide the title compound NMR (DMSO-$d_6$) 1.29 (s, 9H), 1.78–1.90 (m, 1H), 2.43–2.54 (m, 1H, buried under DMSO), 2.76–3.05 (m, 2H), 5.19 (m, 1H), 7.27 (m, 2H), 7.31 (m, 1H), 7.43 (d, 1H), 7.89 (t, 1H), 8.05 (d, 1H), 8.63 (d, 1H), 8.69 (d, 1H), 9.33 (s, 1H), 9.73 (s, 1H); MS (ESI+) 360 (M+H)$^+$; Elemental: Calculated for $C_{23}H_{25}N_3O.HCl.0.5H_2O$: C, 68.22; H, 6.72; N, 10.38. Found: C, 68.31; H, 6.81; N, 10.16.

EXAMPLE 2

N-(5-tert-butyl-2,3-dihydro-1H-inden-1-yl)-N'-(3-methyl-5-isoguinolinyl)urea

EXAMPLE 2A

5-isocyanato-3-methylisoquinoline

The title compound was prepared using the procedure described in Example 1E using 3-methyl-5-isoquinolinamine instead of 5-aminoisoquinoline.

EXAMPLE 2B

N-(5-tert-butyl-2,3-dihydro-1H-inden-1-yl)-N'-(3-methyl-5-isoguinolinyl)urea The title compound was prepared using the procedure described in Example 1F using 5-isocyanato-3-methylisoquinoline instead of 5-isocyanatoisoquinoline. NMR (DMSO-$d_6$) 1.29 (s, 9H), 1.78–1.91 (m, 1H), 2.43–2.53 (m, 1H, buried under DMSO), 2.75 (s, 3H), 2.792.87 (m, 1H), 2.91–3.02 (m, 1H), 5.19 (m, 1H), 7.29 (m, 4H), 7.80 (t, 1H), 7.97 (d, 1H), 8.40 (s, 1H), 8.61 (d, 1H), 9.13 (s, 1H), 9.64 (s, 1H); MS (ESI+) 374 (M+H)$^+$; Elemental: Calculated for $C_{24}H_{27}N_3O.HCl.0.8H_2O$: C, 67.93; H, 7.03; N, 9.90. Found: C, 67.85; H, 7.06; N, 9.66.

EXAMPLE 3

(+) N-(5-tert-butyl-2,3-dihydro-1H-inden-1-yl)-N'-(3-methyl-5-isoguinolinyl)urea Racemic N-(5-tert-butyl-2,3-dihydro-1H-inden-1-yl)-N'-(3-methyl-5-isoquinolinyl)urea was resolved by chiral HPLC using a Chiralcel OD, 20 micron, 5 cm ID×25 cm column with a mobile phase of hexanes (with 0.1% DEA)/ethanol at a 90/10 to 92/8 ratio. The flow rate was 50 ml/min and the sample loading was 100–200 mg per run. $[\alpha]_D$+14.4° (c 1.0; MeOH); NMR (DMSO-$d_6$) 1.29 (s, 9H), 1.78–1.91 (m, 1H), 2.432.53 (m, 1H, buried under DMSO), 2.75 (s, 3H), 2.79–2.87 (m, 1H), 2.91–3.02 (m, 1H), 5.19 (m, 1H), 7.29 (m, 4H), 7.80 (t, 1H), 7.97 (d, 1H), 8.40 (s, 1H), 8.61 (d, 1H), 9.13 (s, 1H), 9.64 (s, 1H); MS (ESI+) 374 (M+H)$^+$; Elemental: Calculated for $C_{24}H_{27}N_3O.HCl.0.9H_2O$: C, 67.64; H, 7.05; N, 9.86. Found: C, 67.77; H, 7.12; N, 9.77.

EXAMPLE 4

(−)N-(5-tert-butyl-2,3-dihydro-1H-inden-1-yl)-N'-(3-methyl-5-isoguinolinyl)urea The title compound was obtained using chiral HPLC as described in Example 3. $[\alpha]_D$−15.3° (c 0.89; MeOH); NMR (DMSO-$d_6$) 1.29 (s, 9H), 1.78–1.91 (m, 1H), 2.43–2.53 (m, 1H, buried under DMSO), 2.75 (s, 3H), 2.79–2.87 (m, 1H), 2.91–3.02 (m, 1H), 5.19 (m, 1H), 7.29 (m, 4H), 7.80 (t, 1H), 7.97 (d, 1H), 8.40 (s, 1H), 8.61 (d, 1H), 9.13 (s, 1H), 9.64 (s, 1H); MS (ESI+) 374 (M+H)$^+$; Elemental: Calculated for $C_{24}H_{27}N_3O.HCl.H_2O$: C, 67.36; H, 7.07; N, 9.82; Found: C, 67.29; H, 7.20; N, 9.91.

EXAMPLE 5

(−) N-(5-tert-butyl-2,3-dihydro-1H-inden-1-yl)-N'-5-isoguinolinylurea

Racemic N-(5-tert-butyl-2,3-dihydro-1H-inden-1-yl)-N'-5-isoquinolinylurea was resolved by chiral HPLC using a Chiralcel OD, 20 micron, 5 cm ID×25 cm column with a mobile phase of hexanes (with 0.1% DEA)/ethanol at a 90/10 to 92/8 ratio, the flow rate was 50 ml/minutes. $[\alpha]_D$−29.4° (c 0.89; MeOH); NMR (DMSO-$d_6$) 1.06 (t, 0.3H (EtOH)), 1.29 (s, 9H), 1.78–1.90 (m, 1H), 2.43–2.54 (m, 1H, buried under DMSO), 2.76–3.05 (m, 2H), 3.44 (q, 0.2H (EtOH)), 5.19 (m, 1H), 7.27 (m, 2H), 7.31 (m, 1H), 7.43 (d, 1H), 7.89 (t, 1H), 8.05 (d, 1H), 8.63 (d, 1H), 8.69 (d, 1H), 9.33 (s, 1H), 9.73 (s, 1H); MS (ESI+) 360 (M+H)$^+$; Elemental: Calculated for $C_{23}H_{25}N_3O.HCl.0.4H_2O.0.1EtOH$: C, 68.34; H, 6.77; N, 10.31. Found: C, 68.44; H, 6.77; N, 10.30.

EXAMPLE 6

(+) N-(5-tert-butyl-2,3-dihydro-1H-inden-1-yl)-N'-5-isoguinolinylurea

Racemic N-(5-tert-butyl-2,3-dihydro-1H-inden-1-yl)-N'-5-isoquinolinylurea was resolved by chiral HPLC using a Chiralcel OD, 20 micron, 5 cm ID×25 cm column with a mobile phase of hexanes (with 0.1% DEA)/ethanol at a 90/10 to 92/8 ratio, the flow rate was 50 ml/minutes. $[\alpha]_D$ +33.3° (c 0.84; MeOH); NMR (DMSO-$d_6$) 1.06 (t, 0.6H (EtOH)), 1.29 (s, 9H), 1.78–1.90 (m, 1H), 2.43–2.54 (m, 1H, buried under DMSO), 2.76–3.05 (m, 2H), 3.44 (q, 0.4H (EtOH)), 5.19 (m, 1H), 7.27 (m, 2H), 7.31 (m, 1H), 7.43 (d, 1H), 7.89 (t, 1H), 8.05 (d, 1H), 8.63 (d, 1H), 8.69 (d, 1H), 9.33 (s, 1H), 9.73 (s, 1H); MS (ESI+) 360 (M+H)$^+$; Elemental: Calculated for $C_{23}H_{25}N_3O \cdot HCl \cdot 0.2H_2O \cdot 0.2EtOH$: C, 68.76; H, 6.81; N, 10.28. Found: C, 68.69; H, 6.83; N, 10.27.

EXAMPLE 7

N-(5-bromo-2,3-dihydro-1H-inden-1-yl)-N'-5-isoguinolinylurea

EXAMPLE 7A 5-bromo-1-indanone O-methyloxime

5-Bromo-1-indanone and O-methylhydroxylamine hydrochloride were combined in pyridine and stirred at ambient temperature for 16 hours. The mixture was concentrated under reduced pressure and the residue was suspended in diethyl ether. The suspension was filtered and the filter cake was washed with diethyl ether. The filtrate was washed with water, 1N HCl, water, and concentrated to provide the title compound. $^1$H NMR (300 MHz, $d_6$-DMSO) 7.63 (m, 2H), 7.48 (m, 2H), 3.90 (s, 3H), 3.00 (m, 2H), 2.80 (m, 2H); MS (DCI/NH$_3$) m/e 240 (M+H)$^+$.

EXAMPLE 7B 5-bromo-1-indanamine

The title compound was prepared using 5-bromo-1-indanone O-methyloxime and the procedure described in Synthesis, 995–996 (1988).

EXAMPLE 7C

N-(5-bromo-2,3-dihydro-1H-inden-1-yl)-N'-5-isoguinolinylurea

The title compound was prepared using the procedure described in Example 1F using 5-bromo-1-indanamine instead of 5-tert-butyl-2,3-dihydro-1H-inden-1-ylamine. $^1$H NMR (300 MHz, $d_6$-DMSO) 9.80 (s, 1H), 9.52 (s, 1H), 8.72 (m, 3H), 808 (d, 1H), 7.90 (t, 1H), 7.67 (d, 1H), 7.49 (m, 1H), 7.40 (m, 1H), 7.31 (d, 1H), 5.20 (m, 1H), 3.022.80 (m, 3H), 1.83 (m, 1H); MS (DCI/NH$_3$) m/e 382 (M+H)$^+$; Anal. Calcd. For $C_{19}H_{16}N_3OBr \cdot 1.0\ HCl \cdot 1.5\ H_2O$: C, 51.20; H, 4.52; N, 9.43. Found: C, 51.21; H, 4.18; N, 8.90.

EXAMPLE 8 methyl 4-({[(5-tert-butyl-2,3-dihydro-1H-inden-1-yl)amino]carbonyl}amino)-1H-indazole-1-carboxylate

EXAMPLE 8A 4-nitro-1H-indazole

2-Methyl-3-nitroaniline (20 g) in acetic acid (~200 mL) was treated with NaNO$_2$ (20 g) in water (50 mL) at 4° C. (mechanical stirring). The reaction mixture was allowed to warm to room temperature and stir overnight. The solvent was removed under reduced pressure. The residue was treated with water (700 mL) and the mixture was filtered. The solid was dried at 45° C. in a vacuum oven overnight to provide the title compound. $^1$H NMR (DMSO) δ 8.56 (s, 1H), 8.2–8.05 (dd, 2H), 7.6 (t, 1H).

EXAMPLE 8B methyl 4-nitro-1H-indazole-1-carboxylate

NaH (0.3 g, 12.5 mmol) in DMF (5 mL) was treated with 4-nitro 1H-indazole (1.33 g, 10 mmol) at 0° C. The reaction mixture was allowed to warm to room temperature and stir for 1 hour. The mixture was treated with methyl chloroformate (0.9 mL) and stirred at room temperature for 3 hours. The mixture was treated with water and filtered to provide the title compound as a solid. $^1$H NMR (300 MHz, DMSO-$d_6$) δ 4.1 9 (s, 3H), 7.9 (t, 1H), 8.38 (d, 1H), 8.62 (d, 1H), 8.85 (s, 1H).

EXAMPLE 8C methyl 4-amino-1H-indazole-1-carboxylate

Methyl 4-nitro-1H-indazole-1-carboxylate 1.66 g, 7.5 mmol) and 10% Pd/C were combined in ethanol (20 mL) and exposed to a hydrogen atmosphere. The reaction mixture was heated at 80° C. for 20 minutes, allowed to cool to room temperature, and filtered through Celite. The filtrate was evaporated to provide title compound. $^1$H NMR (300 MHz, DMSO-$d_6$) δ 6.1 (s, 2H), 6.41 (dd, 1H), 7.21 (m, 2H), 8.42 (s, 1H).

EXAMPLE 8D methyl 4-({[(5-tert-butyl-2,3-dihydro-1H-inden-1-yl)amino]carbonyl}amino)-1H-indazole-1-carboxylate Methyl 4-amino-1H-indazole-1-carboxylate (4.59 g, 24 mmol) in toluene (800 ml) was treated with phosgene (20% in toluene, 25.4 ml, 48 mmol). The mixture was heated at reflux for 3 hours, cooled, and the solvent removed under vacuum. The residue in diethyl ether (800 ml) and triethyl amine (20 ml) was filtered and then treated with 5-tert-butyl-2,3-dihydro-1-inden-1-ylamine (20 mmol, free base prepared from 4.52 g of the HCl salt). After stirring at ambient temperature for 16 hours, the solvent was removed under vacuum and the residue triturated with a 1:1 mixture of diethyl ether and hexanes to provide the title compound. $^1$H NMR (DMSO-$d_6$) δ 1.28 (s, 9H), 1.78–1.91 (m, 1H), 2.39–2.48 (m, 1H), 2.75–2.88 (m, 1H), 2.91–3.02 (m, 1H), 4.04 (s, 3H), 5.17 (m, 1H), 6.73 (d, 1H), 7.27 (s, 2H), 7.30 (m, 1H), 7.50 (m, 1H), 7.69 (d, 1H), 7.88 (d, 1H), 8.41 (s, 1H), 8.87 (s, 1H); MS (ESI+): 407 (M+H)$^+$; Elemental: Calculated for $C_{23}H_{26}N_4O_3 \cdot 0.35Et_2O \cdot 0.15toluene$: C, 68.50; H, 6.93; N, 12.56. Found: C, 68.42; H, 6.66; N, 12.42.

EXAMPLE 9

N-(5-tert-butyl-2,3-dihydro-1H-inden-1-yl)-N'-1H-indazol-4-ylurea

Methyl 4-({[(5-tert-butyl-2,3-dihydro-1H-inden-1-yl)amino]carbonyl}amino)-1H-indazole-1-carboxylate (5.67 g, 14 mmol) in tetrahydrofuran (20 ml) was treated with A 5M solution of sodium hydroxide in methanol (8 ml, 40 mmol). After stirring for 30 minutes, the reaction mixture was diluted with water and filtered. The solid was air-dried and then treated with ethanolic HCl to provide the title compound as the hydrochloride salt. $^1$H NMR (DMSO-d$_6$) δ 1.06 (t, 1.8H, EtOH), 1.27 (s, 9H), 1.75–1.88 (m, 1H), 2.40–2.48 (m, 1H), 2.76–2.88 (m, 1H), 2.90–3.01 (m, 1H), 3.44 (q, 1.2H, EtOH), 5.12 (m, 1H), 6.84 (br d, 1H), 7.05 (d, 1H), 7.20, (m, 1H), 7.26 (s, 2H), 7.31 (s, 1H), 7.69 (d, 1H), 8.10 (s, 1H), 8.70 (s, 1H); MS (ESI+): 349 (M+H)$^+$; Elemental: Calculated for C$_{21}$H$_{24}$N$_4$O.HCl.0.6EtOH.0.6H$_2$O: C, 62.98; H, 7.09; N, 13.23. Found: C, 63.09; H, 6.97; N, 13.18.

EXAMPLE 10 methyl 4-[({[(1S)-5-tert-butyl-2,3-dihydro-1H-inden-1-yl]amino}carbonyl)amino]-1H-indazole-1-carboxylate

EXAMPLE 10A (1S)-5-tert-butyl-2,3-dihydro-1H-inden-1-ylamine 5-tert-Butyl-2,3-dihydro-1H-inden-1-ylamine (25.51 g, 93% potency), N-acetyl-(L)-leucine (23.34 g), and methanol (315 mL) were combined and heated at 65° C. for 1 hour. The solution was allowed to cool to ambient temperature. The solids were filtered and washed with toluene. The solid was then resuspended in methanol (125 mL) and brought to reflux. The solution was allowed to cool to ambient temperature and the solids were filtered. The solid was dried at 40° C. under reduced pressure to provide the title compound (98.7% ee).

EXAMPLE 10B methyl 4-[({[(1S)-5-tert-butyl-2,3-dihydro-1H-inden-1-yl]amino}carbonyl)amino]-1H-indazole-1-carboxylate The title compound was prepared using the procedure in Example 8D, except using (1S)-5-tert-butyl-2,3-dihydro-1H-inden-1-ylamine (free base prepared from the N-acetyl-(L)-Leucine salt), instead of 5-tert-butyl-2,3-dihydro-1H-inden-1-ylamine. $^1$H NMR (DMSO-d$_6$) δ 1.28 (s, 9H), 1.78–1.91 (m, 1H), 2.39–2.48 (m, 1H), 2.75–2.88 (m, 1H), 2.91–3.02 (m, 1H), 4.04 (s, 3H), 5.17 (m, 1H), 6.73 (d, 1H), 7.27 (s, 2H), 7.30 (m, 1H), 7.50 (m, 1H), 7.69 (d, 1H), 7.88 (d, 1H), 8.39 (s, 1H), 8.84 (s, 1H); MS (ESI+): 407 (M+H)$^+$.

EXAMPLE 11 methyl 4-[({[(1R)-5-tert-butyl-2,3-dihydro-1H-inden-1-yl]amino}carbonyl)amino]-1H-indazole-1-carboxylate

EXAMPLE 11A (1S)-5-tert-butyl-2,3-dihydro-1H-inden-1-ylamine 5-tert-Butyl-2,3-dihydro-1H-inden-1-ylamine (11.70 g, 44.4% ee), N-acetyl-(D)-leucine (11.78 g), and methanol (120 mL) were combined and heated at 65° C. for 1 hour. The solution was allowed to cool to ambient temperature. The solids were filtered and washed with toluene. The solid was then resuspended in methanol (125 mL) and brought to reflux. The solution was allowed to cool to ambient temperature and the solids were filtered. The solid was dried at 40° C. under reduced pressure to provide the title compound (98.7% ee).

EXAMPLE 11B methyl 4-[({[(1R)-5-tert-butyl-2,3-dihydro-1H-inden-1-yl]amino}carbonyl)amino]-1H-indazole-1-carboxylate The title compound was prepared using the procedure in Example 8D, except using (1R)-5-tert-butyl-2,3-dihydro-1H-inden-1-ylamine (free base prepared from the N-acetyl-(D)-Leucine salt) instead of 5-tert-butyl-2,3-dihydro-1H-inden-1-ylamine. $^1$H NMR (DMSO-d$_6$) δ 1.28 (s, 9H), 1.78–1.91 (m, 1H), 2.39–2.48 (m, 1H), 2.75–2.88 (m, 1H), 2.91–3.02 (m, 1H), 4.04 (s, 3H), 5.17 (m, 1H), 6.73 (d, 1H), 7.27 (s, 2H), 7.30 (m, 1H), 7.50 (m, 1H), 7.69 (d, 1H), 7.88 (d, 1H), 8.39 (s, 1H), 8.84 (s, 1H); MS (ESI+) 407 (M+H)$^+$; Elemental: Calculated for C$_{23}$H$_{26}$N$_4$O$_3$: C, 67.96; H, 6.45; N, 13.78. Found: C, 67.85; H, 6.51; N, 13.56.

EXAMPLE 12

N-[(1S)-5-tert-butyl-2,3-dihydro-1H-inden-1-yl]-N'-1H-indazol-4-ylurea

The title compound was prepared using the procedure in Example 9, except using methyl 4-[({[(1S)-5-tert-butyl-2,3-dihydro-1H-inden-1-yl]amino}carbonyl)amino]-1H-indazole-1-carboxylate instead of methyl 4-[({[5-tert-butyl-2,3-dihydro-1H-inden-1-yl]amino}carbonyl)amino]-1H-indazole-1-carboxylate. $^1$H NMR (DMSO-d$_6$) δ 1.27 (s, 9H), 1.75–1.88 (m, 1H), 2.40–2.48 (m, 1H), 2.76–2.88 (m, 1H), 2.90–3.01 (m, 1H), 5.15 (m, 1H), 6.84 (br d, 1H), 7.05 (d, 1H), 7.20, (m, 1H), 7.26 (s, 2H), 7.31 (s, 1H), 7.69 (d, 1H), 8.11 (s, 1H), 8.72 (s, 1H); MS (ESI+): 349 (M+H)$^+$; Elemental: Calculated for C$_{21}$H$_{24}$N$_4$O.HCl.0.17hexane: C, 66.19; H, 6.91; N, 14.02. Found: C, 66.11; H, 6.94; N, 13.96

EXAMPLE 13

N-[(1R)-5-tert-butyl-2,3-dihydro-1H-inden-1-yl]-N'-1H-indazol-4-ylurea

The title compound was prepared using the procedure in Example 9, except using methyl 4-[({[(1R)-5-tert-butyl-2,3-dihydro-1H-inden-1-yl]amino}carbonyl)amino]-1H-indazole-1-carboxylate instead of methyl 4-[({[5-tert-butyl-2,3-dihydro-1H-inden-1-yl]amino}carbonyl)amino]-1H-indazole-1-carboxylate. $^1$H NMR (DMSO-d$_6$) δ 1.27 (s, 9H), 1.75–1.88 (m, 1H), 2.40–2.48 (m, 1H), 2.76–2.88 (m, 1H), 2.90–3.01 (m, 1H), 5.15 (m, 1H), 6.84 (br, 1H), 7.05 (d, 1H), 7.20, (m, 1H), 7.26 (s, 2H), 7.31 (s, 1H), 7.69 (d, 1H), 8.17 (s, 1H), 8.83 (s, 1H); MS (ESI+): 349 (M+H)$^+$; Elemental: Calculated for C$_{21}$H$_{24}$N$_4$O.HCl: C, 65.53; H, 6.55; N, 14.56. Found: C, 65.29; H, 6.63; N, 14.23.

EXAMPLE 14 methyl 4-[({[5-(trifluoromethyl)-2,3-dihydro-1H-inden-1-yl]amino}carbonyl)amino]-1H-indazole-1-carboxylate The title compound was prepared using the procedure in Example 8D, except using 5-(trifluoromethyl)-2,3-dihydro- 1H-inden-1-ylamine instead of 5-tert-butyl-2,3-dihydro-1H-inden-1-ylamine. $^1$H NMR (DMSO-d$_6$)δ 1.85–1.98 (m, 1H), 2.50–2.61 (m, 1H), 2.86–2.97 (m, 1H), 3.00–3.12 (m, 1H), 4.04 (s, 3H), 5.29 (m, 1H), 6.85 (d, 1H), 7.51 (m, 1H), 7.57 (m, 2H), 7.64 (s, 1H), 7.70 (d, 1H), 7.85 (d, 1H), 8.42 (s, 1H), 8.96 (s, 1H); MS (ESI+): 419 (M+H)$^+$; Elemental: Calculated for C$_{20}$H$_{17}$N$_4$O$_3$F$_3$: C, 57.42; H, 4.10; N, 13.39. Found: C, 57.44; H, 4.21; N, 13.03.

EXAMPLE 15

N-1H-indazol-4-yl-N'-[5-(trifluoromethyl)-2,3-dihydro-1H-inden-1-yl]urea

The title compound was prepared using the procedure in Example 9, except using methyl 4-[({[5-(trifluoromethyl)-2,3-dihydro-1H-inden-1-yl]amino}carbonyl)amino]-1H-indazole-1-carboxylate instead of methyl 4-[({[5-tert-butyl-2,3-dihydro-1H-inden-1-yl]amino}carbonyl)amino]-1H-indazole-1-carboxylate. $^1$H NMR (DMSO-d$_6$) δ 1.06 (t, 2.4H, EtOH), 1.82–1.94 (m, 1H), 2.52–2.60 (m, 1H), 2.85–2.97 (m, 1H), 2.98–3.10 (m, 1H), 3.44 (q, 1.6H, EtOH), 5.28 (m, 1H), 7.08 (m, 2H), 7.21 (m, 1H), 7.56 (m, 2H), 7.63 (s, 1H), 7.69 (d, 1H), 8.17 (s, 1H), 8.91 (s, 1H); MS (ESI+) 361 (M+H)$^+$; Elemental: Calculated for C$_{18}$H$_{15}$N$_4$OF$_3$.HCl.0.8EtOH.0.1H$_2$O: C, 54.06; H, 4.86; N, 12.87. Found: C, 54.02; H, 4.58; N, 12.62.

EXAMPLE 16 methyl 4-({[(5-piperidin-1-yl-2,3-dihydro-1H-inden-1-yl)amino]carbonyl}amino)-1H-indazole-1-carboxylate

EXAMPLE 16A

5-piperidin-1-ylindan-1-one

5-Fluoroindan-1-one (5 g, 33.3 mmol) and piperidine (8.52 g, 100 mmol, 10 ml) were dissolved in pyridine (20 ml) and heated to reflux for 3 hours. The reaction mixture was cooled, the solvent removed under vacuum, and the residue taken in diethyl ether. The ether solution was washed with 1N aqueous sodium hydroxide and with water, dried with magnesium sulfate, filtered, and the filtrate was removed under vacuum to provide the title compound which was used without further purification. $^1$H NMR (CDCl$_3$) δ 1.67 (m, 6H), 2.63 (m, 2H), 3.02 (m, 2H), 3.40 (m, 4H), 6.78 (d, 1H), 6.86 (dd, 1H), 7.62 (d, 1H); MS (DCI) 216 (M+H)$^+$.

EXAMPLE 16B

5-piperidin-1-ylindan-1-one O-methyloxime

5-Piperidin-1-ylindan-1-one (4.31 g, 20 mmol) in pyridine (20 ml) was treated with methoxyamine hydrochloride (1.84 g, 22 mmol). After stirring at ambient temperature for 40 hours, the solvent was removed under vacuum and the residue taken in water and extracted with diethyl ether. The combined organic layers were washed with water, dried with magnesium sulfate, filtered, and the filtrate was removed under vacuum to provide the title compound which was used without further purification. $^1$H NMR (CDCl$_3$) δ 1.56–1.73 (m, 6H), 2.78–2.89 (m, 1H), 2.91–3.02 (m, 1H), 3.20–3.30 (m, 2H), 3.95 (s, 3H), 6.78 (m, 1H), 6.84 (m, 1H), 7.54 (d, 1H); MS (DCI): 245 (M+H)$^+$.

EXAMPLE 16C

5-piperidin-1-yl-2,3-dihydro-1H-inden-1-ylamine

5-Piperidin-1-ylindan-1-one O-methyloxime (2.95 g, 12 mmol), 10% palladium on carbon (1.45 g), and 20% ammonia in methanol (80 ml), were placed in a Parr apparatus which was charged with hydrogen to 60 psi. The mixture was shaken for 1 hour at ambient temperature and filtered. The filtrate was removed under vacuum to provide the title compound which was used without further purification. $^1$H NMR (CDCl$_3$) δ 1.53–1.60 (m, 2H), 1.65–1.79 (m, 4H), 2.42–2.53 (m, 1H), 2.69–2.81 (m, 1H), 2.86–2.96 (m, 1H), 3.12 (t, 4H), 4.31 (t, 1H), 6.82 (m, 2H), 7.20 (d, 1H); MS (DCI) 217 (M+H)$^+$.

EXAMPLE 16D methyl 4-({[(5-piperidin-1-yl-2,3-dihydro-1H-inden-1-yl)amino]carbonyl}amino)-1H-indazole-1-carboxylate The title compound was prepared using the procedure in Example 8D, except using 5-piperidin-1-yl-2,3-dihydro-1H-inden-1-ylamine instead of 5-tert-butyl-2,3-dihydro-1H-inden-1-ylamine. 1H NMR (DMSO-d$_6$) δ 1.48–1.66 (m, 6H), 1.75–1.89 (m, 1H), 2.39–2.47 (m, 1H), 2.70–2.82 (m, 1H), 2.85–2.95 (m, 1H), 3.10 (m, 4H), 4.04 (s, 3H), 6.61 (d, 1H), 6.81 (m, 2H), 7.12 (d, 1H), 7.49 (m, 1H), 7.68 (d, 1H), 7.88 (d, 1H), 8.38 (s, 1H), 8.82 (s, 1H); MS (ESI+) 434 (M+H)$^+$; Elemental: Calculated for C$_{24}$H$_{27}$N$_5$O$_3$.3CH$_2$Cl$_2$: C, 63.59; H, 6.06; N, 15.26. Found: C, 63.68; H, 6.02; N, 15.14.

EXAMPLE 17

N-1H-indazol-4-yl-N'-(5-piperidin-1-yl-2,3-dihydro-1H-inden-1-yl)urea

The title compound was prepared using the procedure in Example 9, except using methyl 4-({[(5-piperidin-1-yl-2,3-dihydro-1H-inden-1-yl)amino]carbonyl}amino)-1H-indazole-1-carboxylate instead of methyl 4-[({[5-tert-butyl-2,3-dihydro-1H-inden-1-yl]amino}carbonyl)amino]-1H-indazole-1-carboxylate. $^1$H NMR (DMSO-d$_6$) δ 1.09 (t, 1.2H, Et$_2$O), 1.40–2.20 (br m, 7H), 2.52–2.59 (m, 1H), 2.84–2.96 (m, 1H), 2.96–3.07 (m, 1H), 3.38 (q, 0.8H, Et2O), 3.52 (m, 4H), 5.24 (m, 1H), 5.76 (s, 0.2H, CH$_2$Cl$_2$), 7.05 (d, 1H), 7.21 (m, 1H), 7.33 (m, 1H), 7.50 (d, 1H), 7.65–7.77 (m, 3H), 8.29(s, 1H), 9.15 (s, 1H); MS (ESI+) 376 (M+H)$^+$; Elemental: Calculated for C$_{22}$H$_{25}$N$_5$O.2HCl.0.1CH$_2$Cl$_2$.0.2Et$_2$O: C, 58.31; H, 6.24; N, 14.85. Found: C, 58.22; H, 6.54; N, 15.00.

EXAMPLE 18 methyl 4-({[(5-hexahydro-1H-azepin-1-yl-2,3-dihydro-1H-inden-1-yl)amino]carbonyl}amino)-1H-indazole-1-carboxylate

EXAMPLE 18A

5-hexahydro-1H-azepin-1-ylindan-1-one

5-Fluoroindan-1-one (5 g, 33.3 mmol) and azepane (9.92 g, 100 mmol) were dissolved in pyridine (20 ml) and heated at reflux for 3 hours, stirred at ambient temperature for 16 hours, and then heated at reflux for an additional 6 hours.

The solvent was removed under vacuum and the residue partitioned between methylene chloride and water. The organic layer was washed with 1N aqueous sodium hydroxide, dried with magnesium sulfate, filtered, and the filtrate was concentrated under vacuum. The residue was filtered through a pad of silica gel with 1:1 ethyl acetate:hexanes, and the solvent evaporated under vacuum to provide the title compound which was used without further purification. $^1$H NMR (CDCl$_3$) δ 1.56 (m, 4H), 1.81 (m, 4H), 2.62 (m, 2H), 3.02 (m, 2H), 3.55 (t, 4H), 6.59 (d, 1H), 6.68 (dd, 1H), 7.61 (d, 1H); MS (DCI) 230(M+H)$^+$.

EXAMPLE 18B 5-hexahydro-1H-azepin-1-ylindan-1-one O-methyloxime

The title compound was prepared using the procedure in Example 16B, except using 5-hexahydro-1H-azepin-1-ylindan-1-one instead of 5-piperidin-1-ylindan-1-one. 1H NMR (CDCl$_3$) δ 1.55 (m, 4H), 1.79 (m, 4H), 2.77–2.88 (m, 1H), 2.92–3.00 (m, 1H), 3.48 (m, 2H), 3.94 (s, 3H), 6.55 (m, 1H), 6.61 (m, 1H), 7.51 (d, 1H) MS (DCI): 259 (M+H)$^+$.

EXAMPLE 18C 5-hexahydro-1H-azepin-1-yl-2,3-dihydro-1H-inden-1-ylamine

The title compound was prepared using the procedure in Example 16C, except using 5-hexahydro-1H-azepin-1-ylindan-1-one O-methyloxime instead of 5-piperidin-1-ylindan-1-one O-methyloxime. $^1$H NMR (CDCl$_3$) δ 1.55 (m, 4H), 1.60–1.74 (m, 1H), 1.77 (m, 4H), 2.41–2.52 (m, 1H), 2.69–2.69 (m, 1H), 2.86–2.97 (m, 1H), 3.43 (t, 4H), 4.31 (t, 1H), 6.57 (m, 2H), 7.16 (d, 1H); MS (DCI) 231 (M+H)$^+$.

EXAMPLE 18D methyl 4-({[(5-hexahydro-1H-azepin-1-yl-2,3-dihydro-1H-inden-1-yl)amino]carbonyl}amino)-1H-indazole-1carboxylate The title compound was prepared using the procedure in Example 16D, except using 5-hexahydro-1H-azepin-1-yl-2,3-dihydro-1H-inden-1-ylamine instead of 5-piperidin-1-yl-2,3-dihydro-1H-inden-1-ylamine. $^1$H NMR (DMSO-d$_6$) δ 1.17 (t, 0.21H, EtOAc), 1.45 (m, 4H), 1.71 (m, 4H), 1.76–1.86 (m, 1H), 1.99 (s, 0.21H, EtOAc), 2.35–2.48 (m, 1H), 2.69–2.80 (m, 1H), 2.84–2.95 (m, 1H), 3.45 (t, 4H), 4.03 (q, 0.14H, EtOAc), 4.04 (s, 3H), 5.06 (m, 1H), 6.56 (m, 3H), 7.12 (d, 2H), 7.50 (m, 1H), 7.67 (d, 1H), 7.89 (d, 1H), 8.38 (s, 1H). 8.79 (s, 1H); MS (ESI+) 448 (M+H)$^+$; Elemental: Calculated for C$_{25}$H$_{29}$N$_5$O$_3$·0.07EtOAc: C, 66.92; H, 6.57; N, 15.44. Found: C, 66.62; H, 6.85; N, 15.70.

EXAMPLE 19

N-(5-hexahydro-1H-azepin-1-yl-2,3-dihydro-1H-inden-1-yl)-N'-1H-indazol-4-ylurea

The title compound was prepared using the procedure in Example 9, except using methyl 4-({[(5-hexahydro-1H-azepin-1-yl-2,3-dihydro-1H-inden-1-yl)amino]carbonyl}amino)-1H-indazole-1-carboxylate instead of methyl 4-[({[5-tert-butyl-2,3-dihydro-1H-inden-1-yl]amino}carbonyl)amino]-1H-indazole-1-carboxylate. $^1$H NMR (DMSO-d$_6$) δ 1.45 (m, 4H), 1.71 (m, 4H), 1.75–1.81 (m, 1H), 2.38–2.45 (m, 1H), 2.86–2.93 (m, 1H), 3.45 (t, 4H), 5.07 (m, 1H), 6.58 (m, 3H), 7.05 (d, 1H), 7.12 (d, 1H), 7.21 (m, 1H), 7.68 (d, 1H), 8.03 (s, 1H), 8.51 (s, 1H), 12.97 (s, 1H); MS (ESI+) 390 (M+H)$^+$.

EXAMPLE 20

N-1H-indazol-4-yl-N'-[(1R)-5-piperidin-1-yl-2,3-dihydro-1H-inden-1-yl]urea

The title compound was obtained from the preparative chiral separation (ChiralPak AD, Hex(0.2% diethylamine):EtOH:MeOH=8:1:1) of N-1H-indazol-4-yl-N'-(5-piperidin-1-yl-2,3-dihydro-1H-inden-1-yl)urea. $^1$H NMR (300 MHz, d$_6$-DMSO) 13.00 (broad s, 1H), 8.60 (s, 1H), 8.04 (s, 1H), 7.67 (d, 1H), 7.18 (m, 2H), 7.03 (d, 1H), 6.80 (m, 2H), 6.66 (d, 1H), 5.05 (m, 1H), 3.10 (m, 4H), 2.78 (m, 1H), 2.41 (m, 1H), 1.80 (m, 1H), 1.68–1.45 (m, 7H); MS (DCI/NH$_3$) m/e 376 (M+H)$^+$.

EXAMPLE 21

N-1H-indazol-4-yl-N'-[(1S)-5-piperidin-1-yl-2,3-dihydro-1H-inden-1-yl]urea

The title compound was obtained from the preparative chiral separation (ChiralPak AD, Hex(0.2% diethylamine):EtOH:MeOH=8:1:1) of N-1H-indazol-4-yl-N'-(5-piperidin-1-yl-2,3-dihydro-1H-inden-1-yl)urea. $^1$H NMR (300 MHz, d$_6$-DMSO) δ 13.00 (broad s, 1H), 8.61 (s, 1H), 8.04 (s, 1H), 7.67 (d, 1H), 7.18 (m, 2H), 7.03 (d, 1H), 6.80 (m, 2H), 6.66 (d, 1H), 5.05 (m, 1H), 3.10 (m, 4H), 2.78 (m, 1H), 2.41 (m, 1H), 1.80 (m, 1H), 1.68–1.45 (m, 7H); MS (DCI/NH$_3$) m/e 376 (M+H)$^+$.

EXAMPLE 22 isopropyl 4-({[(5-tert-butyl-2,3-dihydro-1H-inden-1-yl)amino]carbonyl}amino)-1H-indazole-1-carboxylate

EXAMPLE 22A isopropyl 4-nitro-1H-indazole-1-carboxylate

The title compound was prepared using the procedure in Example 8B, except using isopropyl chloroformate instead of methyl chloroformate.

EXAMPLE 22B isopropyl 4-amino-1H-indazole-1-carboxylate

The title compound was prepared using the procedure in Example 8C, except using isopropyl 4-nitro-1H-indazole-1-carboxylate instead of methyl 4-nitro-1H-indazole-1-carboxylate.

EXAMPLE 22C isopropyl 4-({[(5-tert-butyl-2,3-dihydro-1H-inden-1-yl)amino]carbonyl}amino)-1H-indazole-1-carboxylate The title compound was prepared using the procedure in Example 8D, except using isopropyl 4-amino-1H-indazole- 1-carboxylate instead of methyl 4-amino-1H-indazole-1-carboxylate. $^1$H NMR (300 MHz, d$_6$-DMSO) 8.82 (s, 1H), 8.40 (s, 1H), 7.90 (d, 1H), 7.68 (d, 1H), 7.50 (m, 1H), 7.29 (d, 2H), 6.67 (d, 1H), 5.20 (m, 2H), 2.92 (m, 1H), 2.8 (m, 1H), 2.41 (m, 1H), 1.84 (m, 1H), 1.40 (d, 6H), 1.30 (s, 9H); MS (DCI/NH$_3$) m/e 435 (M+H)$^+$; Anal. Calcd. For C$_{25}$H$_{30}$N$_4$O$_3$: C, 69.10; H, 6.96; N, 12.89. Found: C, 68.89; H, 6.90; N, 12.83.

EXAMPLE 23 isobutyl 4-({[(5-tert-butyl-2,3-dihydro-1H-inden-1-yl)amino]carbonyl}amino)-1H-indazole-1-carboxylate

EXAMPLE 23A isobutyl 4-nitro-1H-indazole-1-carboxylate

The title compound was prepared using the procedure in Example 8B, except using isobutyl chloroformate instead of methyl chloroformate.

EXAMPLE 23B isobutyl 4-amino-1H-indazole-1-carboxylate

The title compound was prepared using the procedure in Example 8C, except using isobutyl 4-nitro-1H-indazole-1-carboxylate instead of methyl 4-nitro-1H-indazole-1-carboxylate.

EXAMPLE 23C isobutyl 4-({[(5-tert-butyl-2,3-dihydro-1H-inden-1-yl)amino]carbonyl}amino)-1H-indazole-1-carboxylate The title compound was prepared using the procedure in Example 8D, except using isobutyl 4-amino-1H-indazole-1-carboxylate instead of methyl 4-amino-1H-indazole-1-carboxylate. $^1$H NMR (300 MHz, d$_6$-DMSO) 8.82 (s, 1H), 8.40 (s, 1H), 7.90 (d, 1H), 7.68 (d, 1H), 7.50 (m, 1H), 7.29 (d, 2H), 6.70 (d, 1H), 5.19 (m, 1H), 4.23 (d, 2H), 2.88 (m, 1H), 2.80 (m, 1H), 2.41 (m, 1H), 2.10 (m, 1H), 1.84 (m, 1H), 1.40 (d, 6H), 1.27 (s, 9H), 1.00 (d, 6H); MS (DCI/NH$_3$) m/e 435 (M+H)$^+$; Anal. Calcd. For C$_{26}$H$_{32}$N$_4$O$_3$ 0.2 Et$_2$O: C, 69.47; H, 7.40; N, 12.09. Found: C 69.49; H 7.72; N 12.21.

It is understood that the Examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

In Vitro Data

Determination of Inhibition Potencies

Dulbecco's modified Eagle medium (D-MEM)(with 4.5 mg/mL glucose) and fetal bovine serum were obtained from Hyclone Laboratories, Inc. (Logan, Utah). Dulbecco's phosphate-buffered saline (D-PBS)(with 1 mg/mL glucose and 3.6 mg/l Na pyruvate)(without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy)methyl ester) was purchased from Molecular Probes (Eugene, Oreg.).

The cDNAs for the human VR1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 88: 205–215, 2000). The resulting cDNA PCR products were subcloned into pClneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hVR1 cDNA were transfected individually into 1321N1 human astrocytoma cells using Lipofectamine™. Forty-eight hours after transfection, the neomycin-resistant cells were selected with growth medium containing 800 µg/mL Geneticin (Gibco BRL). Surviving individual colonies were isolated and screened for VR1 receptor activity. Cells expressing recombinant homomeric VR1 receptors were maintained at 37° C. in D-MEM containing 4 mM L-glutamine, 300 µg/mL G418 (Cal-biochem) and 10% fetal bovine serum under a humidified 5% CO$_2$ atmosphere.

The functional activity of compounds at the VR1 receptor was determined with a Ca$^{2+}$ influx assay and measurement of intracellular Ca$^{2+}$ levels ([Ca$^{2+}$]i). All compounds were tested over an 11-point half-log concentration range. Compound solutions were prepared in D-PBS (4× final concentration), and diluted serially across 9&well v-bottom tissue culture plates using a Biomek 2000 robotic automation workstation (Beckman-Coulter, Inc., Fullerton, Calif.). A 0.2 µM solution of the VR1 agonist capsaicin was also prepared in D-PBS. The fluorescent Ca$^{2+}$ chelating dye fluo-4 was used as an indicator of the relative levels of [Ca$^{2+}$]i in a 96-well format using a Fluorescence Imaging Plate Reader (FLIPR)(Molecular Devices, Sunnyvale, Calif.). Cells were grown to confluency in 96-well black-walled tissue culture plates. Then, prior to the assay, the cells were loaded with 100 µL per well of fluo-4 AM (2 µM, in D-PBS) for 1–2 hours at 23° C. Washing of the cells was performed to remove extracellular fluo-4 AM (2×1 mL D-PBS per well), and afterward, the cells were placed in the reading chamber of the FLIPR instrument. 50 µL of the compound solutions were added to the cells at the 10 second time mark of the experimental run. Then, after a 3 minute time delay, 50 µL of the capsaicin solution was added at the 190 second time mark (0.05 µM final concentration)(final volume=200 µL) to challenge the VR1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 µM capsaicin (control) response. Curve-fits of the data were solved using a four-parameter logistic Hill equation in GraphPad Prism® (GraphPad Software, Inc., San Diego, Calif.), and $IC_{50}$ values were calculated.

The compounds of the present invention were found to be antagonists of the vanilloid receptor subtype 1 (VR1) receptor with $IC_{50s}$ from about 220 nM to about 1.0 nM. In a preferred range, compounds tested had $IC_{50s}$ from about 50 nM to about 1.0 nM.

In Vivo Data

Determination of Antinociceptive Effect

Experiments were performed on 400 adult male 129J mice (Jackson Laboratories, Bar Harbor, Me.), weighing 20–25 g. Mice were kept in a vivarium, maintained at 22° C., with a 12 hour alternating light-dark cycle with food and water available ad libitum. All experiments were performed during the light cycle. Animals were randomly divided into separate groups of 10 mice each. Each animal was used in one experiment only and was sacrificed immediately following the completion of the experiment. All animal handling and experimental procedures were approved by an IACUC Committee.

The antinociceptive test used was a modification of the abdominal constriction assay described in Collier, et al., Br. J. Pharmacol. Chemother. 32 (1968) 295–310. Each animal received an intraperitoneal (i.p.) injection of 0.3 mL of 0.6% acetic acid in normal saline to evoke writhing. Animals were placed separately under clear cylinders for the observation and quantification of abdominal constriction. Abdominal constriction was defined as a mild constriction and elongation passing caudally along the abdominal wall, accompanied by a slight twisting of the trunk and followed by bilateral extension of the hind limbs. The total number of abdominal constrictions was recorded from 5 to 20 minutes after acetic acid injection. The $ED_{50s}$ were determined based on the i.p. injection.

The compounds of the present invention tested were found to have antinociceptive effects with $ED_{50s}$ from about 1 mg/kg to about 500 mg/kg.

The in vitro and in vivo data demonstrates that compounds of the present invention antagonize the VR1 receptor and are useful for treating pain.

Compounds of the present invention are also useful for ameliorating or preventing additional disorders such as, but not limited to, infammatory thermal hyperalgesia, bladder overactivity, and urinary incontinence as described by Nolano, M. et al., Pain 81 (1999) 135; Caterina, M. J. and Julius, D., Annu. Rev. Neurosci. 24, (2001) 487–517; Caterina, M. J. et al., Science 288 (2000) 306–313; Caterina, M. J. et al., Nature 389 (1997) 816–824; Fowler, C. Urology 55 (2000) 60; and Davis, J. et al., Nature 405 (2000) 183–187.

The present invention also provides pharmaceutical compositions that comprise compounds of the present invention. The pharmaceutical compositions comprise compounds of the present invention that may be formulated together with one or more non-toxic pharmaceutically acceptable carriers.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

The term "pharmaceutically acceptable carrier," as used herein, means a nontoxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I), for example, by hydrolysis in blood.

The present invention contemplates compounds of formula I formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of the compounds of this invention administered to a human or lower animal may range from about 0.01 to about 100 mg/kg/day. For purposes of oral administration, more preferable doses can be in the range of from about 0.1 to about 25 mg/kg/day. If desired, the effective daily dose can be divided into multiple doses for purposes of administration; consequently, single dose compositions may contain such amounts or submultiples thereof to make up the daily dose.

What is claimed is:

1. A compound of formula (I)

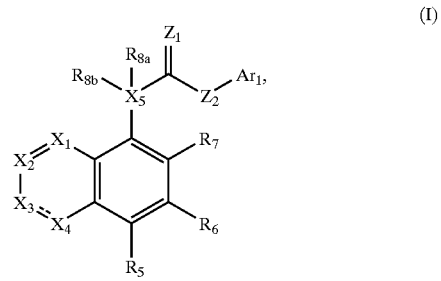

or a pharmaceutically acceptable salt or prodrug thereof, wherein
- - - is absent or a single bond;
$X_1$ is N or $CR_1$;
$X_2$ is N or $CR_2$;
$X_3$ is N, $NR_3$, or $CR_3$;
$X_4$ is a bond, N, or $CR_4$;
$X_5$ is N;
provided that at least one of $X_1$, $X_2$, $X_3$, and $X_4$ is N;
$Z_1$ is O;
$Z_2$ is NH;
$Ar_1$ is dihydro-1H-indenyl, 1H-indenyl, tetrahydronaphthalenyl, or dihydronaphthalenyl, wherein the $Ar_1$ group is optionally substituted with 1, 2, 3, 4, or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, formyl, formylalkyl, haloalkoxy, haloalkyl, haloalkylthio, halogen, heterocycle, hydroxy, hydroxyalkyl, mercapto, mercaptoalkyl, nitro, $(CF_3)_2(HO)C-$, $-NR_AS(O)_2R_B$, $-S(O)_2OR_A$, $-S(O)_2R_B$, $-NZ_AZ_B$, $(NZ_AZ_B)$alkyl, $(NZ_AZ_B)$carbonyl, $(NZ_AZ_B)$carbonylalkyl or $(NZ_AZ_B)$sulfonyl, wherein $Z_A$ and $Z_B$ are each independently hydrogen, alkyl, alkylcarbonyl, formyl, aryl, or arylalkyl;

$R_1$, $R_3$, $R_5$, $R_6$, and $R_7$ are each independently hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C-$, $-NR_AS(O)_2R_B$, $-S(O)_2OR_A$, $-S(O)_2R_B$, $-NZ_AZ_B$, $(NZ_AZ_B)$alkyl, $(NZ_AZ_B)$carbonyl, $(NZ_AZ_B)$carbonylalkyl or $(NZ_AZ_B)$sulfonyl;

R₂ and R₄ are each independently hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C—$, $—NR_AS(O)_2R_B$, $—S(O)_2OR_A$, $—S(O)_2R_B$, $—NZ_AZ_B$, $(NZ_AZ_B)$alkyl, $(NZ_AZ_B)$alkylcarbonyl, $(NZ_AZ_B)$carbonyl, $(NZ_AZ_B)$carbonylalkyl, $(NZ_AZ_B)$sulfonyl, $(NZ_AZ_B)C(=NH)—$, $(NZ_AZ_B)C(=NCN)NH—$, or $(NZ_AZ_B)C(=NH)NH—$;

$R_A$ is hydrogen or alkyl;

$R_B$ is alkyl, aryl, or arylalkyl;

$R_{8a}$ is hydrogen or alkyl; and $R_{8b}$ is absent.

2. The compound according to claim 1 wherein
- - - is a single bond;
$X_1$ is $CR_1$;
$X_2$ is $CR_2$;
$X_4$ is $CR_4$;
$X_3$ is N; and
$Ar_1$ is dihydro-1H-indenyl optionally substituted with 1 or 2 substituents independently selected from alkyl or halogen.

3. The compound according to claim 1 wherein
- - - is a single bond;
$X_1$ is $CR_1$;
$X_2$ is $CR_2$;
$X_4$ is $CR_4$;
$X_3$ and $X_5$ are is N;
$Ar_1$ is 2,3-dihydro-1H-inden-1-yl optionally substituted with 1 or 2 substituents independently selected from alkyl or halogen;
$R_1$, $R_4$, $R_5$, $R_6$, $R_7$, and $R_{8a}$ are hydrogen; and
$R_2$ is hydrogen or alkyl.

4. The compound according to claim 3 that is
N-(5-tert-butyl-2,3-dihydro-1H-inden-1-yl)-N'-5-isoquinolinylurea;
N-(5-tert-butyl-2,3-dihydro-1H-inden-1-yl)-N'-(3-methyl-5-isoquinolinyl)urea;
(+) N-(5-tert-butyl-2,3-dihydro-1H-inden-1-yl)-N'-(3-methyl-5-isoquinolinyl)urea;
(−) N-(5-tert-butyl-2,3-dihydro-1H-inden-1-yl)-N'-(3-methyl-5-isoquinolinyl)urea;
(−) N-(5-tert-butyl-2,3-dihydro-1H-inden-1-yl)-N'-5-isoquinolinylurea;
(+) N-(5-tert-butyl-2,3-dihydro-1H-inden-1-yl)-N'-5-isoquinolinylurea; or
N-(5-bromo-2,3-dihydro-1H-inden-1-yl)-N'-5-isoquinolinylurea.

5. The compound according to claim 1 wherein
- - - is a single bond;
$X_1$ is $CR_1$;
$X_2$ is $CR_2$;
$X_4$ is $CR_4$;
$X_3$ is N; and
$Ar_1$ is 2,3-dihydro-1H-inden-1-yl optionally substituted with 1 or 2 substituents independently selected from alkyl or halogen.

6. The compound according to claim 1 wherein
- - - is a single bond;
$X_1$ is $CR_1$;
$X_2$ is $CR_2$;
$X_4$ is $CR_4$;
$X_3$ and $X_5$ are is N; and $Z_1$ is O;
$Z_2$ is NH;
$Ar_1$ is tetrahydronaphthalenyl optionally substituted with 1 or 2 substituents independently selected from alkyl or halogen.

7. The compound according to claim 1 wherein
- - - is a single bond;
$X_1$ is $CR_1$;
$X_2$ is $CR_2$;
$X_4$ is $CR_4$;
$X_3$ is N;
$Ar_1$ is tetrahydronaphthalenyl optionally substituted with 1 or 2 substituents independently selected from alkyl or halogen;
$R_1$, $R_4$, $R_5$, $R_6$, $R_7$, and $R_{8a}$ are hydrogen; and
$R_2$ is hydrogen or alkyl.

8. The compound according to claim 1 wherein
- - - is a single bond;
$X_1$ is $CR_1$;
$X_2$ is $CR_2$;
$X_4$ is $CR_4$;
$X_3$ is N; and
$Ar_1$ is dihydronaphthalenyl optionally substituted with 1 or 2 substituents independently selected from alkyl or halogen.

9. The compound according to claim 1 wherein
- - - is a single bond;
$X_1$ is $CR_1$;
$X_2$ is $CR_2$;
$X_4$ is $CR_4$;
$X_3$ is N;
$Ar_1$ is dihydronaphthalenyl optionally substituted with 1 or 2 substituents independently selected from alkyl or halogen;
$R_1$, $R_4$, $R_5$, $R_6$, $R_7$, and $R_{8a}$ are hydrogen; and
$R_2$ is hydrogen or alkyl.

10. The compound according to claim 1 wherein
- - - is absent;
$X_1$ is $CR_1$;
$X_2$ is N;
$X_3$ is $NR_3$;
$X_4$ is a bond; and
$Ar_1$ is 2,3-dihydro-1H-inden-1-yl optionally substituted with 1 or 2 substituents independently selected from alkyl, haloalkyl, halogen, or heterocycle.

11. The compound according to claim 1 wherein
- - - is absent;
$X_1$ is $CR_1$;
$X_2$ is N;
$X_3$ is $NR_3$;
$X_4$ is a bond;
$Ar_1$ is 2,3-dihydro-1H-inden-1-yl optionally substituted with 1 or 2 substituents independently selected from alkyl, haloalkyl, halogen, or heterocycle, wherein the heterocycle is piperidinyl or hexahydro-1H-azepinyl; and
$R_3$ is hydrogen.

12. The compound according to claim 11 that is
N-(5-tert-butyl-2,3-dihydro-1H-inden-1-yl)-N'-1H-indazol-4-ylurea;
N-[(1S)-5-tert-butyl-2,3-dihydro-1H-inden-1-yl]-N'-1H-indazol-4-ylurea;
N-[(1R)-5-tert-butyl-2,3-dihydro-1H-inden-1-yl]-N'-1H-indazol-4-ylurea;
N-1H-indazol-4-yl-N'-[5-(trifluoromethyl)-2,3-dihydro-1H-inden-1-yl]urea;

N-1H-indazol-4-yl-N'-(5-piperidin-1-yl-2,3-dihydro-1H-inden-1-yl)urea;

N-(5-hexahydro-1H-azepin-1-yl-2,3-dihydro-1H-inden-1-yl)-N'-1H-indazol-4-ylurea;

N-1H-indazol-4-yl-N'-[(1R)-5-piperidin-1-yl-2,3-dihydro-1H-inden-1-yl]urea; or

N-1H-indazol-4-yl-N'-[(1S)-5-piperidin-1-yl-2,3-dihydro-1H-inden-1-yl]urea.

13. The compound according to claim 1 wherein
- - - is absent;
$X_1$ is $CR_1$;
$X_2$ is N;
$X_3$ is $NR_3$;
$X_4$ is a bond;
$Ar_1$ is 2,3-dihydro-1H-inden-1-yl optionally substituted with 1 or 2 substituents independently selected from alkyl, haloalkyl, halogen, or heterocycle, wherein the heterocycle is piperidinyl or hexahydro-1H-azepinyl; and
$R_3$ is alkoxycarbonyl.

14. The compound according to claim 13 that is methyl 4-({[(5-tert-butyl-2,3-dihydro-1H-inden-1-yl)amino]carbonyl}amino)-1H-indazole-1-carboxylate;

methyl 4-[({[(1S)-5-tert-butyl-2,3-dihydro-1H-inden-1-yl]amino}carbonyl)amino]-1H-indazole-1-carboxylate;

methyl 4-[({[(1R)-5-tert-butyl-2,3-dihydro-1H-inden-1-yl]amino}carbonyl)amino]-1H-indazole-1-carboxylate;

methyl 4-[({[5-(trifluoromethyl)-2,3-dihydro-1H-inden-1-yl]amino}carbonyl)amino]-1H-indazole-1-carboxylate;

methyl 4-({[(5-piperidin-1-yl-2,3-dihydro-1H-inden-1-yl)amino]carbonyl}amino)-1H-indazole-1-carboxylate;

methyl 4-({[(5-hexahydro-1H-azepin-1-yl-2,3-dihydro-1H-inden-1-yl)amino]carbonyl}amino)-1H-indazole-1-carboxylate;

isopropyl 4-({[(5-tert-butyl-2,3-dihydro-1H-inden-1-yl)amino]carbonyl}amino)-1H-indazole-1-carboxylate; or isobutyl 4-({[(5-tert-butyl-2,3-dihydro-1H-inden-1-yl)amino]carbonyl}amino)-1H-indazole-1-carboxylate.

15. A pharmaceutical composition comprising a therapeutically effective amount of a compound of formula (I) as defined in claim 1, or a pharmaceutically acceptable salt or prodrug thereof.

* * * * *